(12) United States Patent
Knudson et al.

(10) Patent No.: US 9,586,046 B2
(45) Date of Patent: Mar. 7, 2017

(54) ELECTRODE BAND SYSTEM AND METHODS OF USING THE SYSTEM TO TREAT OBESITY

(71) Applicant: EnteroMedics Inc., St. Paul, MN (US)

(72) Inventors: Mark B. Knudson, Shoreview, MN (US); Richard R. Wilson, Arden Hills, MN (US); Katherine S. Tweden, Mahtomedi, MN (US); Timothy R. Conrad, Eden Prairie, MN (US)

(73) Assignee: Enteromedics, Inc., St. Paul, MN (US)

( * ) Notice: Subject to any disclaimer, the term of this patent is extended or adjusted under 35 U.S.C. 154(b) by 0 days.

(21) Appl. No.: 14/480,242

(22) Filed: Sep. 8, 2014

(65) Prior Publication Data

US 2015/0012065 A1    Jan. 8, 2015

Related U.S. Application Data

(63) Continuation of application No. 13/758,223, filed on Feb. 4, 2013, now Pat. No. 8,862,233, which is a
(Continued)

(51) Int. Cl.
*A61N 1/36* (2006.01)
*A61N 1/05* (2006.01)
(Continued)

(52) U.S. Cl.
CPC ........ *A61N 1/36053* (2013.01); *A61F 5/0026* (2013.01); *A61N 1/05* (2013.01); *A61N 1/321* (2013.01); *A61N 1/36007* (2013.01); *A61N 1/36071* (2013.01); *A61N 1/36082* (2013.01); *A61N 1/37235* (2013.01)

(58) Field of Classification Search
None
See application file for complete search history.

(56) References Cited

U.S. PATENT DOCUMENTS 3,128,760 A    4/1964 Baker
3,411,507 A    11/1968 Wingrove
(Continued)

FOREIGN PATENT DOCUMENTS

EP    0076070        4/1983
EP    0896828 A2    2/1999
(Continued)

OTHER PUBLICATIONS

"Bravo™ pH Monitoring System Catheter-Free pH Testing", document No. UC 200300235 EN N15344, Medtronic, Inc., Minneapolis, Minnesota, USA (2002).
(Continued)

*Primary Examiner* — Brian T Gedeon
*Assistant Examiner* — Ankit D Tejani
(74) *Attorney, Agent, or Firm* — Merchant & Gould P.C.

(57) ABSTRACT

At least one of a plurality of disorders of a patient characterized at least in part by vagal activity innervating at least one of a plurality of organs of the patient is treated by a method that includes positioning an electrode on a vagus nerve. An electrical signal is applied to the electrode to modulate vagal activity by an amount selected to treat the disorder. In some embodiments, the disorder is obesity. The signal may be a blocking or a stimulation signal. In some embodiments, the signal is selected to, at least in part, downregulate neural activity on the vagus nerve.

4 Claims, 12 Drawing Sheets

Related U.S. Application Data continuation of application No. 13/178,221, filed on Jul. 7, 2011, now Pat. No. 8,369,952, which is a continuation of application No. 11/656,121, filed on Jan. 22, 2007, now Pat. No. 7,986,995, which is a continuation of application No. 10/752,944, filed on Jan. 6, 2004, now Pat. No. 7,167,750, which is a continuation-in-part of application No. 10/674,330, filed on Sep. 29, 2003, now Pat. No. 7,489,969, and a continuation-in-part of application No. 10/675,818, filed on Sep. 29, 2003, now abandoned, and a continuation-in-part of application No. 10/674,324, filed on Sep. 29, 2003, now abandoned, said application No. 10/674,330 is a continuation-in-part of application No. 10/358,093, filed on Feb. 3, 2003, now abandoned, said application No. 10/675,818 is a continuation-in-part of application No. 10/358,093, filed on Feb. 3, 2003, now abandoned, said application No. 10/674,324 is a continuation-in-part of application No. 10/358,093, filed on Feb. 3, 2003, now abandoned.

(51) Int. Cl.
*A61N 1/32* (2006.01)
*A61F 5/00* (2006.01)
*A61N 1/372* (2006.01)

(56) References Cited

U.S. PATENT DOCUMENTS

| | | | |
|---|---|---|---|
| 4,114,625 A | 9/1978 | Onat |
| 4,198,963 A | 4/1980 | Barkalow et al. |
| 4,315,503 A | 2/1982 | Ryaby et al. |
| 4,541,432 A | 9/1985 | Molina-Negro et al. |
| 4,702,254 A | 10/1987 | Zabara |
| 4,776,349 A | 10/1988 | Nashef et al. |
| 4,867,164 A | 9/1989 | Zabara |
| 5,025,807 A | 6/1991 | Zabara |
| 5,188,104 A | 2/1993 | Wernicke et al. |
| 5,199,430 A | 4/1993 | Fang et al. |
| 5,215,086 A | 6/1993 | Terry, Jr. et al. |
| 5,226,429 A | 7/1993 | Kuzmak |
| 5,231,988 A | 8/1993 | Wernicke et al. |
| 5,263,480 A | 11/1993 | Wernicke et al. |
| 5,269,303 A | 12/1993 | Wernicke et al. |
| 5,292,344 A | 3/1994 | Douglas |
| 5,299,569 A | 4/1994 | Wernicke et al. |
| 5,330,515 A | 7/1994 | Rutecki et al. |
| 5,335,657 A | 8/1994 | Terry et al. |
| 5,344,438 A | 9/1994 | Testerman |
| 5,370,675 A | 12/1994 | Edwards et al. |
| 5,423,872 A | 6/1995 | Cigaina |
| 5,437,291 A | 8/1995 | Pasricha et al. |
| 5,514,175 A | 5/1996 | Kim et al. |
| 5,540,730 A | 7/1996 | Terry, Jr. et al. |
| 5,571,150 A | 11/1996 | Wernicke et al. |
| 5,601,604 A | 2/1997 | Vincent |
| 5,620,955 A | 4/1997 | Knight et al. |
| 5,690,691 A | 11/1997 | Chen et al. |
| 5,707,400 A | 1/1998 | Terry, Jr. et al. |
| 5,716,385 A | 2/1998 | Mittal et al. |
| 5,747,060 A | 5/1998 | Sackler |
| 5,749,907 A | 5/1998 | Mann |
| 5,830,434 A | 11/1998 | Taylor et al. |
| 5,836,994 A | 11/1998 | Bourgeois |
| 5,861,014 A | 1/1999 | Familoni |
| 5,919,216 A | 7/1999 | Houben et al. |
| 5,967,977 A | 10/1999 | Mullis et al. |
| 5,995,872 A | 11/1999 | Bourgeois |
| 6,002,964 A | 12/1999 | Feler et al. |
| 6,083,249 A | 7/2000 | Familoni |
| 6,091,992 A | 7/2000 | Bourgeois et al. |
| 6,093,167 A | 7/2000 | Houben et al. |
| 6,097,984 A | 8/2000 | Douglas |
| 6,098,629 A | 8/2000 | Johnson et al. |
| 6,104,955 A | 8/2000 | Bourgeois |
| 6,111,715 A | 8/2000 | Tsuchiya et al. |
| 6,129,726 A | 10/2000 | Edwards |
| 6,135,978 A | 10/2000 | Houben et al. |
| 6,148,222 A | 11/2000 | Ramsey, III |
| 6,216,039 B1 | 4/2001 | Bourgeois |
| 6,238,423 B1 | 5/2001 | Bardy |
| 6,243,607 B1 | 6/2001 | Mintchev et al. |
| 6,261,280 B1 | 7/2001 | Houben et al. |
| 6,261,572 B1 | 7/2001 | Donovan |
| 6,290,961 B1 | 9/2001 | Aoki et al. |
| 6,292,703 B1 | 9/2001 | Meier et al. |
| 6,308,105 B1 | 10/2001 | Duysens et al. |
| 6,312,708 B1 | 11/2001 | Donovan |
| 6,341,236 B1 | 1/2002 | Osorio et al. |
| 6,364,899 B1 | 4/2002 | Dobak, III |
| 6,369,079 B1 | 4/2002 | Rubin et al. |
| 6,405,732 B1 | 6/2002 | Edwards et al. |
| 6,418,346 B1 | 7/2002 | Nelson et al. |
| 6,449,511 B1 | 9/2002 | Mintchev et al. |
| 6,473,644 B1 | 10/2002 | Terry, Jr. et al. |
| 6,532,388 B1 | 3/2003 | Hill et al. |
| 6,558,708 B1 | 5/2003 | Lin |
| 6,571,127 B1 | 5/2003 | Ben-Haim et al. |
| 6,587,719 B1 | 7/2003 | Barrett et al. |
| 6,587,725 B1 | 7/2003 | Durand et al. |
| 6,591,137 B1 | 7/2003 | Fischell |
| 6,600,956 B2 | 7/2003 | Maschino et al. |
| 6,609,025 B2 | 8/2003 | Barrett et al. |
| 6,610,713 B2 | 8/2003 | Tracey |
| 6,611,715 B1 | 8/2003 | Boveja |
| 6,612,983 B1 | 9/2003 | Marchal |
| 6,622,038 B2 | 9/2003 | Barrett et al. |
| 6,684,105 B2 | 1/2004 | Cohen et al. |
| 6,746,474 B2 | 6/2004 | Saadat |
| 6,760,626 B1 | 7/2004 | Boveja |
| 6,826,428 B1 | 11/2004 | Chen et al. |
| 6,832,114 B1 | 12/2004 | Whitehurst et al. |
| 6,853,862 B1 | 2/2005 | Marchal et al. |
| 6,879,859 B1 | 4/2005 | Boveja |
| 6,895,278 B1 | 5/2005 | Gordon |
| 6,901,295 B2 | 5/2005 | Sharma |
| 6,928,320 B2 | 8/2005 | King |
| 6,985,773 B2 | 1/2006 | Von arx et al. |
| 6,993,391 B2 | 1/2006 | Flesler et al. |
| 7,054,690 B2 | 5/2006 | Imran |
| 7,072,720 B2 | 7/2006 | Puskas |
| 7,076,307 B2 | 7/2006 | Boveja et al. |
| 7,142,910 B2 | 11/2006 | Puskas |
| 7,167,750 B2 | 1/2007 | Knudson et al. |
| 7,292,890 B2 | 11/2007 | Whitehurst et al. |
| 7,299,091 B2 | 11/2007 | Barrett |
| 7,310,557 B2 | 12/2007 | Maschino et al. |
| 7,317,948 B1 | 1/2008 | King et al. |
| 7,340,306 B2 | 3/2008 | Barrett |
| 7,343,539 B2 | 3/2008 | Divsalar et al. |
| 7,346,398 B2 | 3/2008 | Gross et al. |
| 7,389,145 B2 | 6/2008 | Kilgore et al. |
| 7,444,183 B2 | 10/2008 | Knudson |
| 7,444,184 B2 | 10/2008 | Boveja |
| 7,489,969 B2 | 2/2009 | Knudson et al. |
| 7,551,960 B2 | 6/2009 | Forsberg et al. |
| 7,613,515 B2 | 11/2009 | Knudson |
| 7,620,454 B2 | 11/2009 | Dinsmoor et al. |
| 7,620,455 B2 | 11/2009 | Maschino |
| 7,630,769 B2 | 12/2009 | Knudson et al. |
| 7,672,727 B2 | 3/2010 | Donders et al. |
| 7,693,577 B2 | 4/2010 | Knudson et al. |
| 7,706,875 B2 | 4/2010 | Buras et al. |
| 7,720,539 B2 | 5/2010 | Mintchev |
| 7,720,540 B2 | 5/2010 | Knudson et al. |
| 7,729,771 B2 | 6/2010 | Knudson |
| 7,734,355 B2 | 6/2010 | Cohen et al. |
| 7,738,961 B2 | 6/2010 | Sharma |
| 7,742,818 B2 | 6/2010 | Dinsmoor et al. |
| 7,822,486 B2 | 10/2010 | Foster et al. |

(56) References Cited

U.S. PATENT DOCUMENTS

| | | |
|---|---|---|
| 7,844,338 B2 | 11/2010 | Knudson et al. |
| 7,917,226 B2 | 3/2011 | Nghiem et al. |
| 7,986,995 B2 | 7/2011 | Knudson et al. |
| 8,010,204 B2 | 8/2011 | Knudson |
| 8,046,085 B2 | 10/2011 | Knudson et al. |
| 8,068,918 B2 | 11/2011 | Vallapureddy et al. |
| 8,103,399 B2 | 1/2012 | Davis et al. |
| 8,140,167 B2 | 3/2012 | Donders et al. |
| 8,239,027 B2 | 8/2012 | Imran |
| 8,260,426 B2 | 9/2012 | Armstrong et al. |
| 2001/0012828 A1 | 8/2001 | Aoki et al. |
| 2001/0051787 A1 | 12/2001 | Haller et al. |
| 2002/0016617 A1 | 2/2002 | Oldham |
| 2002/0032468 A1 | 3/2002 | Hill et al. |
| 2002/0052336 A1 | 5/2002 | Yerxa et al. |
| 2002/0055779 A1 | 5/2002 | Andrews |
| 2002/0072780 A1 | 6/2002 | Foley |
| 2002/0087192 A1 | 7/2002 | Barrett et al. |
| 2002/0094962 A1 | 7/2002 | Ashley et al. |
| 2002/0103424 A1 | 8/2002 | Swoyer et al. |
| 2002/0161360 A1 | 10/2002 | Carroll |
| 2002/0198570 A1 | 12/2002 | Puskas |
| 2002/0198571 A1 | 12/2002 | Puskas |
| 2003/0014086 A1 | 1/2003 | Sharma |
| 2003/0018367 A1 | 1/2003 | DiLorenzo |
| 2003/0040785 A1 | 2/2003 | Maschino et al. |
| 2003/0045909 A1 | 3/2003 | Gross et al. |
| 2003/0045914 A1 | 3/2003 | Cohen et al. |
| 2003/0074039 A1 | 4/2003 | Puskas |
| 2003/0135245 A1 | 7/2003 | Campos |
| 2003/0135248 A1 | 7/2003 | Stypulkowski |
| 2003/0144708 A1 | 7/2003 | Starkebaum |
| 2003/0144709 A1 | 7/2003 | Zabara et al. |
| 2003/0171789 A1 | 9/2003 | Malek et al. |
| 2003/0181958 A1 | 9/2003 | Dobak, III |
| 2003/0181959 A1 | 9/2003 | Dobak, III |
| 2003/0195601 A1 | 10/2003 | Hung et al. |
| 2003/0212440 A1 | 11/2003 | Boveja |
| 2004/0015201 A1 | 1/2004 | Greenstein |
| 2004/0039425 A1 | 2/2004 | Greenwood-van Meerveld |
| 2004/0059383 A1 | 3/2004 | Puskas |
| 2004/0086531 A1 | 5/2004 | Barron |
| 2004/0089313 A1 | 5/2004 | Utley et al. |
| 2004/0111126 A1 | 6/2004 | Tanagho et al. |
| 2004/0127953 A1 | 7/2004 | Kilgore et al. |
| 2004/0167583 A1 | 8/2004 | Knudson et al. |
| 2004/0172084 A1 | 9/2004 | Knudson et al. |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0176812 A1 | 9/2004 | Knudson et al. |
| 2004/0181178 A1 | 9/2004 | Aldrich et al. |
| 2004/0193229 A1 | 9/2004 | Starkebaum et al. |
| 2004/0199214 A1 | 10/2004 | Merfeld et al. |
| 2004/0230255 A1 | 11/2004 | Dobak, III |
| 2004/0236381 A1 | 11/2004 | Dinsmoor et al. |
| 2004/0236382 A1 | 11/2004 | Dinsmoor et al. |
| 2004/0243182 A1 | 12/2004 | Cohen et al. |
| 2004/0249416 A1 | 12/2004 | Yun et al. |
| 2004/0254616 A1 | 12/2004 | Rossing et al. |
| 2005/0021101 A1 | 1/2005 | Chen et al. |
| 2005/0038484 A1 | 2/2005 | Knudson et al. |
| 2005/0049655 A1 | 3/2005 | Boveja et al. |
| 2005/0070970 A1 | 3/2005 | Knudson et al. |
| 2005/0070974 A1 | 3/2005 | Knudson et al. |
| 2005/0075684 A1 | 4/2005 | Phillips et al. |
| 2005/0075693 A1 | 4/2005 | Toy et al. |
| 2005/0131485 A1 | 6/2005 | Knudson et al. |
| 2005/0137644 A1 | 6/2005 | Boveja et al. |
| 2005/0143378 A1 | 6/2005 | Yun et al. |
| 2005/0143412 A1 | 6/2005 | Puskas |
| 2005/0143787 A1 | 6/2005 | Boveja et al. |
| 2005/0149141 A1 | 7/2005 | Starkebaum |
| 2005/0149146 A1 | 7/2005 | Boveja et al. |
| 2005/0149148 A1 | 7/2005 | King |
| 2005/0192644 A1 | 9/2005 | Boveja et al. |
| 2005/0203501 A1 | 9/2005 | Aldrich et al. |
| 2005/0240231 A1 | 10/2005 | Aldrich et al. |
| 2005/0267542 A1 | 12/2005 | David et al. |
| 2006/0015151 A1 | 1/2006 | Aldrich |
| 2006/0030919 A1 | 2/2006 | Mrva et al. |
| 2006/0036293 A1 | 2/2006 | Whitehurst et al. |
| 2006/0041277 A1 | 2/2006 | Deem |
| 2006/0100668 A1 | 5/2006 | Ben-David et al. |
| 2006/0161217 A1 | 7/2006 | Jaax et al. |
| 2006/0190053 A1 | 8/2006 | Dobak, III |
| 2006/0212089 A1 | 9/2006 | Tass et al. |
| 2006/0229685 A1 | 10/2006 | Knudson et al. |
| 2006/0247722 A1 | 11/2006 | Maschino et al. |
| 2006/0247737 A1 | 11/2006 | Olson et al. |
| 2007/0027484 A1 | 2/2007 | Guzman et al. |
| 2007/0043400 A1 | 2/2007 | Donders et al. |
| 2007/0100377 A1 | 5/2007 | Armstrong et al. |
| 2007/0191912 A1 | 8/2007 | Fischer et al. |
| 2007/0203521 A1 | 8/2007 | Dobak et al. |
| 2007/0239226 A1 | 10/2007 | Overstreet |
| 2008/0021512 A1 | 1/2008 | Knudson et al. |
| 2008/0086179 A1 | 4/2008 | Sharma |
| 2008/0103533 A1 | 5/2008 | Patel et al. |
| 2008/0147137 A1 | 6/2008 | Cohen et al. |
| 2008/0195171 A1 | 8/2008 | Sharma |
| 2008/0221644 A1 | 9/2008 | Vallapureddy et al. |
| 2008/0275514 A1 | 11/2008 | Ben-David et al. |
| 2008/0300654 A1 | 12/2008 | Lambert et al. |
| 2008/0300657 A1 | 12/2008 | Stultz |
| 2009/0187230 A1 | 7/2009 | Dilorenzo |
| 2009/0210019 A1 | 8/2009 | Kim et al. |
| 2009/0275997 A1 | 11/2009 | Faltys et al. |
| 2009/0306465 A1 | 12/2009 | Dudai |
| 2009/0306739 A1 | 12/2009 | Dilorenzo |
| 2010/0094375 A1 | 4/2010 | Donders et al. |
| 2010/0241183 A1 | 9/2010 | DiLorenzo |
| 2010/0292754 A1 | 11/2010 | Gliner |
| 2011/0013084 A1 | 1/2011 | Black |
| 2011/0071589 A1 | 3/2011 | Starkebaum et al. |
| 2012/0022608 A1 | 1/2012 | Libbus et al. |
| 2012/0022617 A1 | 1/2012 | Tockman et al. |
| 2012/0053653 A1 | 3/2012 | Hiernaux et al. |
| 2012/0059431 A1 | 3/2012 | Williams et al. |
| 2012/0065698 A1 | 3/2012 | Errico et al. |
| 2012/0071946 A1 | 3/2012 | Errico et al. |
| 2012/0078319 A1 | 3/2012 | De Ridder |
| 2012/0083855 A1 | 4/2012 | Gross et al. |
| 2012/0101874 A1 | 4/2012 | Ben-Haim et al. |
| 2012/0136408 A1 | 5/2012 | Grill et al. |
| 2012/0232610 A1 | 9/2012 | Soffer et al. |
| 2012/0239108 A1 | 9/2012 | Foutz et al. |
| 2012/0253378 A1 | 10/2012 | Makower et al. |
| 2012/0259380 A1 | 10/2012 | Pyles |

FOREIGN PATENT DOCUMENTS

| | | |
|---|---|---|
| EP | 1004330 A1 | 5/2000 |
| EP | 0865800 | 9/2004 |
| EP | 1666087 A1 | 7/2006 |
| WO | 01/41671 A2 | 6/2001 |
| WO | 01/43821 A1 | 6/2001 |
| WO | 02/26320 A1 | 4/2002 |
| WO | 02/065896 | 8/2002 |
| WO | 2004/036377 A2 | 4/2004 |
| WO | 2004/064918 A1 | 8/2004 |
| WO | 2004/082763 A1 | 9/2004 |
| WO | 2004/093981 | 11/2004 |
| WO | 2004/110551 A2 | 12/2004 |
| WO | 2006/023498 | 3/2006 |
| WO | 2009/131639 A1 | 10/2009 |
| WO | 2012/044472 A2 | 4/2012 |
| WO | 2012/060874 A2 | 5/2012 |

OTHER PUBLICATIONS

"Medical Care for Obese Patients", U.S. Department of Health and Human Services, National Institute of Diabetes and Digestive and

(56) References Cited

OTHER PUBLICATIONS

Kidney Diseases, pp. 1-6, NIH Publication No. 03-5335, (Feb. 2003).
Accarino et al., "Symptomatic Responses to Stimulation of Sensory Pathways In The Jejunum", Am. J. Physiol., 263:G673-G677 (1992).
Accarino et al., "Selective Dysfunction of Mechano Sensitive Intestinal Afferents In Irritable Bowel Syndrome", Gastroenterology, 108:636-643 (1994).
Accarino et al., "Attention and Distraction Colon Affects on Gut Perception", Gastroenterology, 113:415-442 (1997).
Accarino et al., "Modification of Small Bowel Mechanosensitivity by Intestinal Fat", GUT, 48:690-695 (2001).
Accarino et al., "Gut Perception In Humans Is Modulated by Interacting Gut Stimuli", Am. J. Physiol. Gastrointestinal Liver Physiol., 282:G220-G225 (2002).
Aggarwal et al., "Predominant Symptoms in Irritable Bowel Syndrome Correlate with Specific Autonomic Nervous system Abnormalities", Gastroenterol, 106:945-950 (1994).
Amaris et al., "Microprocessor controlled movement of solid colonic content using sequential neural electrical stimulation", Gut, 50:475-479 (2002).
Balaji et al., "A Safe and Noninvasice Test for Vagal Integrity Revisited", Archive Surgery, 137:954-959 (2002).
Balemba et al., "Innervation of the extrahepatic biliary tract", The Anatomical Record Part A: Discoveries in Molecular, Cellular, and Evolutionary Biology; 280A(1):836-847 (2004).
Bard® Minnesota Four Lumen Esophagogastric Tamponade Tube for the Control of Bleeding from Esophageal Varices (Instructions for Use), C. R. Bard, Inc., Covington, GA, USA (1998).
Baron, et al., "Acute Necrotizing Pancreatitis", *New England J. of Medicine*, vol. 340, No. 18, pp. 1412-1417 (1999).
Batterham et al., "Inhibition of Food Intake in Obese Subjects by Peptide $YY_{3-36}$", New England J. Med., 349:941-948 (Sep. 4, 2003).
Beglinger et al., "Postprandial Control of Gallbladder Contraction and Exocrine Pancreatic Secretion in Man", Euro. J. of Clinical Investigation, 22(12):827-834 (Jan. 1993).
Bell et al., "The Interplay between Hydrogen Ions, Bicarbonate Ions and Osmolality in the Anterior Duodenuym Modulating Gastric Function in the Conscious Calf", J. Physiol., 314(1):331-341 (May 1, 1981).
Benini, "Gastric Emptying and Dyspeptic Symptoms in Patients with Gastroesophageal Reflux", Amer. J. of Gastroenterology, 91(7):1351-1354 (Jul. 1996).
Benini et al., "Omeprazole Causes Delay in Gastric Emptying of Digestible Meals", *Digestive Diseases and Sciences*, 41(3):469-474 (Mar. 1996).
Berthoud et al., "Characteristics of Gastric and Pancreatic Reponses to Vagal Stimulation with Varied Frequencies: Evidence for Different Fiber Calibers?", J. Auto. Nervous Sys., 19(1):77-84 (1987).
Biron et al., "Clinical Experience with Biliopancreatic Bypass and Gastrectomy or Selective Vagotomy for Morbid Obesity", Canadian J. of Surg., 29(6):408-410 (Dec. 1986).
Boss et al., Laparoscopic Truncal Vagotomy for Severe Obesity: Six Month Experience in 10 Patients from a Prospective, Two-Center Study, Proceedings of the 24th Annual Meeting, American Society for Metabolic & Bariatric Surgery, Plenary Session Abstracts, (Abstract No. 44) (Jun. 2007) (reprinted from http://www.asbs.org/archive/abstracts/plenary_edited_2007.pdf).
Bourde et al., "Vagal Stimulation: II. Its Effect on Pancreatic Secretion in Conscious Dogs", Annals of Surgery, 171(3):357-364 (Mar. 1970).
Bowen, "Secretion of Bile and the Role of the Bile Acids in Digestion", Hypertexts for Biomedical Sciences Pathophysiology of the Digestive System, Colorado State University (Mar. 10, 2001) (downloaded from http://arbl.cvmbs.colostate.edu/hbooks/pathphys/digestion/liver/bile.html.).
Brancatisano et al., "Implantation Technique of a Novel Vagal Blockade Medical Device for the Treatment of Obesity," IFSO-APC OSSANZ Conference 2008: Mar. 25-27, 2009, Hilton Cairns, Queensland Conference Program Handbook.
Brancatisano et al., "Empower: A 12-Month Randomized, Prospective Clinical Trial: Safety and Effectiveness of VBLOC Therapy," 23rd Annual Scientific Conference of the Obesity Surgery Society of Australia and New Zealand, OSSANZ Conference 2010: The Changing Shape of Bariatrics, Nov. 10-12, Wednesday Nov. 10, 10:30 am-12 noon, Tasmania Hotel Grand Chancellor, Hobart, Conference Program Handbook.
Burneo et al., "Weight Loss Associated With Vagus Nerve Stimulation", Neurology, 59(3):463-464 (Aug. 13, 2002).
Camilleri et al., "Determinants of Response to a Prokinetic Agent in Neuropathic Chronic Intestinal Motility Disorder", American Gastroenterological Association, 106(4):916-923 (1994).
Camilleri et al., "Vagal Blocking for Obesity control (VBLOC): Plasma Pancreatic Polypeptide (PPP) Response to a Standardized Sham Meal Challenge," The Obesity Society 2007 Annual Scientific Meeting, Oct. 20-24, 2007, New Orleans Louisiana. Supplement to Obesity, vol. 15, Program Abstract Supplement, (Sep. 2007).
Camilleri et al., "Intra-abdominal Vagal Blocking (VBLOC therapy): Clinical Results with a New Implantable Medical Device," Surgery, 143(6):723-731 (Jun. 2008).
Camilleri et al., "Selection of Electrical Algorithms to Treat Obesity with Intermittent Vagal Block Using an Implantable Medical Device," Surgery for Obesity and Related Diseases, Official Journal of the American Society for Bariatric Surgery, 5(2):224-229 (Mar./Apr. 2009).
Cann et al., "Irritable Bowel Syndrome: Relationship of Disorders in the Transit of a Single Solid Meal to Symptoms Patterns", Gut, 24(5):405-411 (May 1983).
Chang et al., "Long-Term Results of Duodenectomy with Highly Selective Vagotomy in the Treatment of complicated Duodenal Ulcers", Amer. J. of Surg., 181(4):372-376 (2001).
Chatzicostas et al., "Balthazar computed tomography severity index is superior to Ranson criteria and APACHE II and II scoring systems in predicting acute pancreatitis outcome", J. Clinical Gastroenterology, 36(3):253-260 (2003).
Chey, "Regulation of Pancreatic Exocrine Secretion", Int'l J. of Pancreatology, 9(1):7-20 (Summer 1991).
Chey et al., "Neural Hormonal Regulation of Exocrine Pancreatic Secretion", Pancreatology, 1:320-335 (2001).
Cigaina, "Gastric Pacing as Therapy for Morbid Obesity", Obesity Surgery, 12(Supp 1):12S-16S (Apr. 2002).
Coffin et al, "Somatic Stimulation Reduces Perception of Gut Distention In Humans", Gastroenterology, 107(6):1636-1642 (Dec. 1994).
Collins et al., "Reduces Calorie Intake and Weight Loss during Vagal Block (VBLOC Therapy) in Morbidly Obese Patients with Type 2 Diabetes Mellitus," 23rd Annual Scientific Conference of the Obesity Surgery Society of Australia and New Zealand, OSSANZ Conference 2010: The Changing Shape of Bariatrics, Nov. 10-12, Thurs Nov. 11, 10:30 am-12 noon, Tasmania Hotel Grand Chancellor, Hobart, Conference Program Handbook.
Cuomo et al., "Functional Dyspepsia Symptoms, Gastric Emptying and Satiety Provocation Test: Analysis of Relationships", Scand J Gastroenterol , 36(10):1030-1036 (Oct. 2001).
Cyberonics, Inc 2001 Annual Report, pp. 1, 5-7 and 16 (2001).
Cyberonics, Inc. 2003 Form 10-K to Securities and Exchange Commission, pp. 1 and 10 as printed on May 23, 2006 from http://www.secinfo.com/dsvRu.23yb.htm.
D'Argent, "Gastric Electrical Stimulation: Preliminary Results", Obesity Surgery, 12(Supp 1):21S-25S (Apr. 2002).
Dapoigny et al., "Vagal influence on colonic motor activity in conscious nonhuman primates", Am. J. Physiol., 262: G231-G236 (1992).
Davidson et al., "Long-Term Effects of Botulinum Toxin Injections in Spasmodic Dysphonia", Ann. Otol. Rhinol. Laryngol., 105:34-42 (1996).
DeVault et al., "Updated Guidelines for the Diagnosis and Treatment of Gastroesophageal Reflux Disease", Am J Gastroenterol, 94:1434-1442 (1999).

(56) References Cited

OTHER PUBLICATIONS

Drossman, "Rome II: A Multinational Consensus Document on Gastrointestinal Disorders—The Functional Gastrointestinal Disorders and the Rome II Process", Gut, 45(Suppl II):II1-II5 (1999).
Estevão-Costa et al., "Delayed Gastric Emptying and Gastroesophageal Reflux: A Pathophysiologic Relationship", J. of Pediatric Gastroenterology and Nutrition, pp. 471-474 (2001).
Evans et al., "Jejunal Sensorimotor Dysfunction in Irritable Bowel Syndrome: Clinical and Psychosocial Features", Gastroenterol, 110:393-404 (1996).
Evans et al., "Gastroparesis and Small Bowel Dysmotility in Irritable Bowel Syndrome", Dig Dis Sci., 42:2087-2093 (1997).
Faris et al., "Effect of Decreasing Afferent Vagal Activity with Ondansetron on Symptoms of Bulimia Nervosa: a Randomized, Double-Blind Trial", The Lancet, pp. 792-797 (2000).
Furukawa et al., "Effects of Selective Vagal Stimulation on the Gallbladder and Sphincter of Oddi and Peripheral Vagal Routes Mediating Bile Evacuative Responses Induced by Hypothalamic Stimulation", JJP vol. 42 321-334, (1992).
George, et al., "Vagus Nerve Stimulation Therapy", Neurology, 59(Suppl 4):S56-S61 (2002).
Gershon, "The Second Brain", Harper Collins Publishers, Inc, New York, NY p. 19 (1998).
Gleysteen et al., "Reversible Truncal Vagotomy in Conscious Dogs", Gastroenterology, 85:578-583 (1983).
Görtz et al., "A Five- to Eight-Year Follow-up Study of Truncal Vagotomy as a Treatment for Morbid Obesity", Proceedings of the Third Annual Meeting, American Society for Bariatric Surgery, p. 145 (Abstract) (1986).
Görtz et al., "Truncal Vagotomy Reduces Food and Liquid Intake in Man", Physiology & Behavior, 48:779-781 (1990).
Gray, Anatomy of the Human Body, 13$^{th}$ Ed., C. Clemente, Editor, (Lea & Febiger, Philadelphia, PA USA, Publisher) title pages and p. 69, 70 and 1186 (1985).
Greydanus et al., "Neurohormonal Factors in Functional Dyspepsia: Insights on Pathophysiological Mechanisms", American Gastroenterological Association, 100(5):1311-1318 (1991).
Grossi et al., "Swallows, oesophageal and gastric motility in normal subjects and in patients with gastro-oesophageal reflux disease: a 24-h pH-manometric study," Neurogastroenterol. Mot., 10:115-121 (1998).
Gui et al., "Botulinum Toxin Injected in the Gastric Wall Reduces Body Weight and Food Intake in Rats", Aliment Pharmacol Ther., 14:829-834 (2000).
Guyton et al., "Propulsion and Mixing of Food in the Alimentary Tract", Textbook of Medical Physiology, 10$^{th}$ ed. Philadelphia: W. B. Saunders and Company, 200:728-737.
Guyton AC, et al., "Secretory Functions of the Alimentary Tract", Textbook of Medical Physiology, 10$^{th}$ ed. Philadelphia: W. B. Saunders and Company, 200:738-753.
Hassall et al., "Mechanisms of Gastroesophageal Reflux and Gastroesophageal Reflux Disease", Journal of Pediatric Gastroenterology and Nutrition, 35:119-136 (Aug. 2002).
Hausken et al., "Low Vagal Tone and Antral Dysmotility in Patients with Functional Dyspepsia", Psychosomatic Medicine, 55: 12-22 (1993).
Heitkemper, et al., "Evidence for Automatic Nervous System Imbalance in Women with Irritable Bowel Syndrome", Digestive Diseases and Sciences, 43(9):2093-2098 (1998).
Herrera et al, "Implantation Technique of a Rechargeable Vagal Blocking system for Treatment of Obesity"; Obesity Surgery, 18:946 (2008).
Herrera et al., "Intermittent Vagal Blocking with An Implantable Device Reduces Maximum Tolerated Volume (MTV) During a Standardized Nutrient Drink Test in Obese Subjects," AGA Institute, AASLD, SSAT, The 110th Annual Meeting of the AGA Institute: Digestive Disease Week May 30-Jun. 4, 2009, Chicago, IL, Gastroenterology 136(5)(Suppl. 1) (May 2009).
Herrera et al., "VBLOC and Improvements in Co-Morbidities in Obese Subjects During Weight Loss," Obesity Surgery: The Journal of Metabolic Surgery and Allied Care, Program and Abstracts of the 14th World Congress of IFSO, Paris, France, Aug. 26-29, 2009. An International Surgical Journal for Research and Treatment of Massive Obesity, 19(8):983-984 (Aug. 2009).
Herrera et al., "Intermittent Vagal Blocking with an Implantable Device Reduces Maximum Tolerated Volume (MTV) During a Standardized Nutrient Drink Test in Obese Subjects," Obesity Surgery: The Journal of Metabolic Surgery and Allied Care, Program and Abstracts of the 14th World Congress of IFSO, Paris, France, Aug. 26-29, 2009. An International Surgical Journal for Research and Treatment of Massive Obesity, 19(8):1012 (Aug. 2009).
Herrera et al., "Intermittent Vagal Blockade with an Implantable Device Improves Glycemic Control in Obese subjects with Type 2 Diabetes," 2009 Poster Session / Supplement to Surgery for Obesity and Related Diseases, Official Journal of the American Society for Bariatric Surgery, 5(3S):S48-S49 (May/Jun. 2009).
Herrera et al., "Vagal Blocking Improves Glycemic Control and Blood Pressure in Subjects with Type 2 Diabetes and Hypertension," 2010 Plenary Session / Supplement to Surgery for Obesity and Related Diseases, Official Journal of the American Society for Bariatric Surgery, 2(3):S1-S26 (May/Jun. 2010).
Herrera et al., "Treatment of Obesity-Related Type 2 Diabetes with Vagal Blocking," Obesity 2011 Abstract Supplement / Poster Abstracts—Monday, Oct 3, 2011, Obesity, 19(Supp 1):S185, (Nov. 2011), www.obsesityjournal.org.
Hjelland, et al., "Vagal tone and meal-induced abdominal symptoms in healthy subjects", Digestion, 65: 172-176 (2002).
Holst et al., "Nervous Control of Pancreatic Exocrine Secretion in Pigs", Acta Physiol. Scand., 105(1):33-51 (Jan. 1979).
Holst et al., "Nervous control of pancreatic endocrine secretion in Pigs. I. Insulin and glucagon resopnses to electrical stimulation of the vagus nerves" Acta Physiol Scand, 111(1):1-7 (Jan. 1981).
Hornbuckle et al. "The Diagnosis and Work-Up of the Patient with Gastroparesis", J Clin Gastroenterol, 30:117-124 (2000).
Hunt, "The Relationship Between The Control of pH and Healing and Symptom Relief In Gastro-Oesophageal Reflux Disease", Ailment Pharmacol Ther., 9 (Suppl. 1):3-7 (1995).
ICD-10, "Classification of Mental and Behavioural Disorders", World Health Organization (1992), 2 pages, printed from http://www.mental-health-matters.com/disorders/dis_details.
International Search Report and Written Opinion mailed Dec. 3, 2008.
International Search Report and Written Opinion mailed Jul. 8, 2009.
International Search Report and Written Opinion mailed May 25, 2009.
International Search Report for PCT/US2009/053114 dated Oct. 26, 2009.
International Search Report Partial mailed Aug. 28, 2008.
Kaiser, "Gallstone Ileus", New England J. of Medicine, 336(12):879-880 (1997) (correspondence).
Kaminski et al., "The Effect of Electrical Vagal Stimulation on Canine Pancreatic Exocrine Function", Surgery, 77(4):545-552 (Apr. 1975).
Kellow et al., "Dysmotility of the Small Intestine in Irritable Bowel Syndrome", Gut, 29:1236-1243 (1988).
Kellow et al., "Rome II: A Multinational Consensus Document on Gastrointestinal Disorders—Principles of Applied Neurogastroenterology: Physiology/Motility-Sensation", Gut, 45(Supp II):II17-II24 (1999).
Kilgore et al., "Nerve Conduction Block Utilising High-Frequency Alternating Current," Medical & Biological Engineering & Computing, 42:394-406 (2004).
Koch et al., "Can Plasma Human Pancreatic Polypeptide Be Used to Detect Diseases of the Exocrine Pancreas?", Mayo Clinic Proc., 60:259-265 (Apr. 1985).
Koren et al., "Vagus Nerve Stimulation Does Not Lead to Significant Changes In Body Weight In Patients With Epilepsy", Epilepsy & Behavior, 8:246-249 (2005).
Korner et al., "To Eat or Not to Eat—How the Gut Talks to the Brain", New England J. Med., pp. 926-928 (Sep. 4, 2003).

(56) References Cited

OTHER PUBLICATIONS

Kosel et al., "Beyond the Treatment of Epilepsy: New Applications of Vagus Nerve Stimulation in Psychiatry", CNS Spectrums, 8(7):515-521 (Jul. 2003).
Kow et al., "An Implantable Vagal Blocking System to Treat Obesity: Laparoscopic Implantation Technique and Early Results in a proof-of-Principle Clinical Study,", SAGES 2008 Emerging Technology Oral Abstracts, p. 295, www.sages.org.
Kow et al., "Comparison of Food Ingestion Disorders with Three Devices for Obesity," Obesity Surgery: Including Laparoscopy and Allied Care, Program and Abstracts of the 13th World Congress of IFSO, Buenos Aires, Argentina, Sep. 24-27, 2008. An International Surgical Journal for Research and Treatment of Massive Obesity, 18(8):914-915 (Aug. 2008).
Kow et al., "Selecting Vagal Blocking Electrical Algorithms for Obesity Treatment," Obesity Surgery: Including Laparoscopy and Allied Care, Program and Abstracts of the 13th World Congress of IFSO, Buenos Aires, Argentina, Sep. 24-27, 2008. An International Surgical Journal for Research and Treatment of Massive Obesity, 18(8):924, (Aug. 2008).
Kow et al., "Comparison of Food Ingestion disorders with Three Devices for Obesity Treatment," and Wilson, Richard, et al., "Intra-abdominal Vagal Blocking Reduces Body Weight with Associated Reductions in Heart Rate and Without Adverse Effects on Electrocardiographic Parameters," TOS 2008 Abstract Supplement / Poster Session 2 Abstracts, 16(Supp. 1): S222, (Oct. 2008) www.obesityjournal.org.
Kow et al., "Vagal Blocking for the Treatment of Obesity Delivered Using the Fully Implantable Maestro Rechargeable System: 12 Month Results," Surgery for Obesity and Related Diseases: Emerging Technologies Session 2011, 7:363-364, (2011).
Kow et al., "Vagal Blocking Improves Obesity-Related Co-Morbidities in Obese Subjects with type 2 Diabetes Mellitus," 23rd Annual Scientific Conference of the Obesity Surgery Society of Australia and New Zealand, OSSANZ Conference 2010: The Changing Shape of Bariatrics, Nov. 10-12, Wednesday Nov. 10, 3:30 pm-5:00 pm, Tasmania Hotel Grand Chancellor, Hobart, Conference Program Handbook.
Kral, "Vagotomy as a Treatment for Morbid Obesity", Surg. Clinics ofN. Amer., 59(6):1131-1138 (1979).
Kral, "Vagotomy for Treatment of Severe Obesity", The Lancet, 311(8059):307-308 (Feb. 1978).
Kral et al., "Gastroplasty for Obesity: Long-Term Weight Loss Improved by Vagotomy", World J. Surg., 17(1):75-79 (Jan./Feb. 1993).
Lagergren et al., "Symptomatic Gastroesophageal Reflux as a Risk Factor for Esophageal Adenocarcinoma", New Engl J Med, 340:825-831(1999).
Layer et al., "Human pancreatic secretion during phase II antral motility of the interdigestive cycle", American Physiological Society, 254(2):G249-G253 (Feb. 1, 1988).
Lin et al., "Hardware—software co-design of portable functional gastrointestinal stimulator system", J. of Medical Eng. & Tech., 27(4):164-177 (2003).
Long, editor, Chapter 3, "The Stomach", Gastrointestinal System, $2^{nd}$ Ed., Mosby Publisher, London (2002).
Long, editor, Chapter 4, "The Liver and Biliary Tract", Gastrointestinal System, $2^{nd}$ Ed., Mosby Publisher, London (2002).
Mabayo, et al., "Inhibition of Food Passage by Omeprazole in the Chicken", European J. of Pharmacology, 273(1-2):161-165 (Jan. 1995).
Martin-Portugues, et al., "Histopathologic Features of the Vagus Nerve After Electrical Stimulation in Swine", Histol Histopathol, 20:851-856 (2005).
Medical Encyclopedia: Anorexia Nervosa, U.S. National Library of Medicine and National Institutes of Health, pp. 1-3 (Jun. 22, 2004) printed from http://www.nlm.nih.gov/medlineplus/print/ency/article/000362.htm, (Jun. 6, 2006).

Merio et al., "Slow Gastric Emptying in Type 1 Diabetes: Relation to Autonomic and Peripheral Neuropathy, Blood Glucose, and Glycemic Control", Diabetes Care, 20:419-423 (1997).
Mintchev et al., "Electrogastrographic impact of multi-site functional gastric electrical stimulation", J. of Medical Eng. & Tech., 23(1):5-9 (1999).
Mittal et al., "Mechanism of Disease: The Esophagogastric Junction", New Engl J Med, 336:924-932 (1997).
Mokdad et al., "Prevalence of Obesity, Diabetes, and Obesity-Related Health Risk Factors, 2001", JAMA, 289(1):76-79 (Jan. 1, 2003).
Netter, "Atlas of Human Anatomy", 3rd Ed., Plate 120, (Icon Learning Systems, New Jersey) (2003).
Norton, et al., "Optimizing Outcomes in Acute Pancreatitis", Drugs, 61(11):1581-1591 (2001).
Novartis product description, Zelnorm® (T2002-19) (Jul. 2002).
O'Brien et al., "The Laparoscopic Adjustable Gastric Band (Lap-Band®): A Prospective Study of Medium-Term Effects on Weight, Health and Quality of Life," Obesity Surgery, 12:652-660 (2002).
Owyang, "Negative Feedback Control of Exocrine Pancrfeatic Secretion: Role of Cholecystokinin and Cholinergic Pathway", Symposium: Physiology of Cholecystokinin, American Institute of Nutrition, pp. 1321S-1326S (1994).
Paterson et al., "Determinants of Occurrence and Volume of Transpyloric Flow During Gastric Emptying of Liquids in Dogs: Importance of Vagal Input", Dig Dis Sci, 45:1509-1516 (2000).
Peeters et al., "Obesity in Adulthood and Its Consequences for Life Expectancy: A Life Table Analysis", Annals of Internal Medicine, 138(1):24-32 (2003).
Petrofsky et al., "Impact of Recruitment Order on Electrode Design for Neural Prosthetics of Skeletal Muscle", Am. J. of Physical Medicine, 60(5):243-253 (1981).
Poelmans et al., "Prospective Study on the Incidence of Chronic Ear Complaints Related to Gastroesophageal Reflux and on the Outcome of Antireflux Therapy", Ann Otol Rhinol Laryngol, 111:933-938 (2002).
Product Brochure, "ATROSTIM Phrenic Nerve Stimulator," AtroTech Oy, P.O. Box 28, FIN-33721 Tampere, Finland, 2 pages (Jun. 2004).
Rashev et al., "Microprocessor-Controlled Colonic Peristalsis", Digestive Diseases and Sciences, 47(5):1034-1048 (2002).
Rashev et al., "Three-dimensional static parametric modeling of phasic colonic contractions for the purpose of microprocessor-controlled functional stimulation", J. of Medical Eng. & Tech., 25(3):85-96 (2001).
Rasmussen et al., "A Double-Blind Placebo-Controlled Study on the Effects of Omeprazole on Gut Hormone Secretion and Gastric Emptying Rate", Scand. J. Gastroenterol, 32(9):900-905 (1997).
Rösch et al., "Frequency-Dependent Secretion of Pancreatic Amylase, Lipase, Trypsin, and Chymotrypsin During Vagal Stimulation in Rats", Pancreas, 5(5):499-506 (Sep. 1990).
Roslin et al., "The Use Of Electrical Stimulation of The Vagus Nerve to Treat Morbid Obesity", Epilepsy & Behavior, 2:S11-S16 (2001) at p. S13.
Roslin et al., "Vagus Nerve Stimulation in the Treatment of Morbid Obesity", Vagus Nerve Stimulation, 2nd Ed., 6:113-121 (2003).
Sarnelli et al., "Symptoms Associated with Impaired Gastric Emptying of Solids and Liquids in Functional Dyspepsia", Am J Gastroenterol, (2003) 98:783-788.
Sarr et al., "The Empower Study: Randomized, Prospective, Double-Blind, Multicenter Trial of Vagal Blockade to Induce Weight Loss in Morbid Obesity," Obes. Surg. Published Sep. 8, 2012, (12pp) Springer Science+Business Media, LLC (2012).
Sautter et al., "Transient Paralysis of the Bladder due to Wound Botulism", Eur. Urol., 39:610-612 (2001).
Schapiro et al., "Neurohypophyseal Regulation of the Exocrine Pancreas", Amer. J. of Gastroenterology, 71(6):587-591 (Jun. 1979).
Scheffer et al., "Elicitation of Transient Lower Oesophageal Sphincter Relaxations in Response to Gastric Distension", Neurogastroenterol Motil, 14:647-655 (2002).
Schmidt et al., "Ambulatory 24-Hour Jejunal Motility in Diarrhea-Predominant Irritable Bowel Syndrome", J Gastroenterol, 31:581-589 (1996).

(56) References Cited

OTHER PUBLICATIONS

Schwartz et al., "Human Duodenal Motor Activity in Response to Acid and Different Nutrients", Dig Dis Sci, 46:1472-1481 (2001).
Schwartz et al., "Chemospecific Alterations in Duodenal Perception and Motor Response in Functional Dyspepsia", Am J Gastroenterol, 96:2596-2602 (2001).
Sherman, "Obesity and Technology: Can the stomach be fooled", Reuters (Apr. 26, 2006), 3 pages, http://news.yahoo.com/s/nm/20060426/us_nm/bizfeature_obesity_technology_de&printer as printed on May 23, 2006.
Shikora, "'What are the Yanks Doing?' The U.S. Experience with Implantable Gastric Stimulation (IGS) for the Treatment of Obesity—Update on the Ongoing Clinical Trials", Obes Surg, 14(Supp 1):S40-S48 (Sep. 2004).
Simren et al., "Abnormal Propagation Pattern of Duodenal Pressure Waves in the Irritable Bowel Syndrome (IBS)", Dig Dis Sci, 45:2151-2161 (2000).
Smith et al., "Truncal Vagotomy in Hypothalamic Obesity", The Lancet, 1(8337):1330-1331 (Jun. 11, 1983).
Solomonow et al., "Control of Muscle Contractile Force through Indirect High-Frequency Stimulation", Am. J. of Physical Medicine, 62(2):71-82 (1983).
Sontag et al., "Asthmatics with Gastroesophageal Reflux: Long Term Results of a Randomized Trial of Medical and Surgical Antireflux Therapies", Am J Gastroenterol, 98:987-999 (2003).
Soran et al., "Outcome and quality of life of patients with acute pancreatitis requiring intensive care", J. Surg. Res., 91(1):89-94 (2000).
Stanghellini et al., "Risk Indicators of Delayed Gastric Emptying of Solids in Patients with Functional Dyspepsia", Gastroenterol , 110:1036-1042 (1996).
Steer et al., "Chronic Pancreatitis", New England J. of Medicine, 332:1482-1490 (Jun. 1, 1995).
Steinbrook, "An Opioid Antagonist for Postoperative Ileus", New England J. of Medicine, 345(13):988-989 (2001) (Editorial).
Steinbrook, "Surgery for Severe Obesity", New England J. Med., 350:1075-1079 (2004).
Tack et al., "Role of Impaired Gastric Accommodation to a Meal in Functional Dyspepsia", Gastroenterol, 115:1346-1352 (1998).
Tack et al., "Symptom Pattern and Gastric Emptying Rate Assessed by the Octanoic Acid Breath Test in Functional Dyspepsia" [abstract]. Gastroenterol, 114:A301 (1998).
Taguchi et al., "Selective Postoperative Inhibition of Gastrointestinal Opioid Receptors", New England J. of Medicine, 345(13):935-940 (2001).
Talley et al., "Rome II: A Multinational Consensus Document on Gastrointestinal Disorders—Functional Gastroduodenal Disorders" Gut, 45(Supp II):II37-II42 (1999).
Taylor et al., "Effects of Pancreatic Polypeptide, Caerulein, and Bombesin on Satiety in Obese Mice", American Journal of Physiology, 248:G277-G280 (1985).
Thompson et al., "Rome II: A Multinational Consensus Document on Gastrointestinal Disorders—Functional Bowel Disorders and Functional Abdominal Pain", Gut, 45(Suppl II):II43-II47 (1999).
Tiscornia et al., "Neural Control of the Exocrine Pancreas: An Analysis of the Cholinergic, Adrenergic, and Peptidergic Pathways and Their Positive and Negative Components 1: Neural Mechanisms", Mount Sinai J. of Medicine, 54:366-383 (1987).
Toouli et al., "Vagal Blocking for Obesity Control (VBLOC): Effects on Excess Weight Loss, Calorie Intake, Satiation and Satiety," Obesity Surgery: Including Laparoscopy and Allied Care, Program Issue, World Congress, Porto, Sep. 5-8, 2007. An International Surgical Journal for Research and Treatment of Massive Obesity, 17(8):1043 (Aug. 2007).
Toouli et al., "Intra-Abdominal Vagal Blocking Reduces Calorie Intake, Enhances Satiation and Reduces Hunger during Significant and Sustained Weight Loss in Obese Subjects," Digestive Disease Week and the 109th Annual Meeting of the AGA Institute: May 17-22, 2008, San Diego, CA, Gastroenterology 134(4)(Suppl. 1): A-370 (Apr. 2008).
Toouli et al., "Vagal Blocking for Obesity Control (VBLOC): Interim Six Months Results in an ongoing Trial Using a Second Generation System," 2008 Scientific Session of the Society of American Gastrointestinal and Endoscopic (SAGES), Philadelphia, Pennsylvania, USA Apr. 9-12, 2008. Poster Presentations, Surgical Endoscopy (2008) 22:S194, Springer Science+Business Media, LLC (2008).
Toouli et al., "Vagal Blocking: Treatment of Obesity Related type 2 Diabetes and blood Pressure—18 Month Results," 24th Annual Scientific Conference of the Obesity Surgery Society of Australia and New Zealand, OSSANZ Conference 2012: Bariatric surgery-more than an operation, Apr. 11-13, Wednesday Nov. 11 3:30 pm-5:00 pm, Northern Territory Darwin Convention Centre, Darwin, Conference Program Handbook.
Toouli et al., "Vagal Blocking for Obesity Control (VBLOCTM): Ongoing Comparison of Weight Loss with Two Generations of an Active, Implantable Medical Device," 2008 Plenary Session II / Surgery for Obesity and Related Diseases, Official Journal of the American Society for Bariatric Surgery, e t al., 4(3):305 (May/Jun. 2008).
Toouli et al., "Reduced Calorie Intake and Weight Loss During Vagal Bloc (VBLOC Therapy) in Morbidly Obese Patients with Type 2 Diabetes Mellitus," Gastroenterology, 140: S-619, AGA Institute (2011).
Toouli et al., "Treatment of Obesity-Related Co-Morbidities with VBLOC Therapy," Obes. Surg., 21:998, (2011).
Tweden et al., "Vagal Blocking for Obesity Control (VBLOC): Studies of Pancreatic and Gastric Function and Safety in a Porcine Model," Plenary Session Feb. 2006, Surgery for Obesity and Related Diseases, Official Journal of the American Society for Bariatric Surgery, 2(3):301-302 (May/Jun. 2006).
Tweden et al., "Vagal Blocking for Obesity Control (VBLOC): Studies of Pancreatic Function and Safety in a Porcine Model," Obesity Surgery: Including Laparoscopy and Allied Care, Program Issue, World Congress, Australia, Aug. 30-Sep. 2, 2006. An International Surgical Journal for Research and Treatment of Massive Obesity, 16(8):988 (Aug. 2006).
Tweden et al., "Vagal Blocking for Obesity Control (VBLOC): Concordance of Effects of Very High Frequency Blocking Current at the Neural and Organ Levels Using Two Preclinical Models," Gastroenterology 2006, 130(suppl2 2):A-148, AGA Institute.
Tweden et al., "Vagal Blocking Treatment of Obesity Related Type 2 Diabetes and Blood Pressure—18 Month Results,"5th Congress of the International Federation for the surgery of Obesity and Metabolic Disorders European Chapter (IFSO-EC), Barcelona '12, Apr. 26-28, 2012.
Tougas, "The Autonomic Nervous System in Functional Bowel Disorders", Gut, vol. 47 (Suppl IV):iv78-iv80 (2000).
Tzu-Ming et al., "Long-Term Results of Duodenectomy with Highly Selective Vagotomy in the Treatment of complicated Duodenal Ulcers", Amer. J. of Surg., 181:372-376 (2001).
Undeland et al., "Wide Gastric Antrum and Low Vagal Tone in Patients with Diabetes Mellitus Type 1 Compared to Patients with Functional Dyspepsia and Healthy Individuals", Dig Dis Sci, 41:9-16 (1996).
U.S. Appl. No. 10/674,330 Office Action mailed Apr. 22, 2008.
U.S. Appl. No. 11/040,767 Notice of Allowance dated Jun. 22, 2009.
U.S. Appl. No. 11/656,113 Office Action dated Apr. 6, 2009.
U.S. Appl. No. 11/656,113 Notice of Allowance dated Dec. 7, 2009.
U.S. Appl. No. 11/656,122 Notice of Allowance dated Aug. 7, 2009.
U.S. Appl. No. 11/656,123 Office Action dated Dec. 10, 2009.
U.S. Appl. No. 11/656,132 Office Action dated Jul. 20, 2009.
U.S. Appl. No. 11/891,770 Office Action dated Jul. 20, 2009.
U.S. Appl. No. 11/891,770 Notice of Allowance dated Feb. 1, 2010.
U.S. Appl. No. 12/721,603, filed Mar. 11, 2010.
U.S. Appl. No. 12/908,375, filed Oct. 20, 2010.
Van Den Honed et al., "Generation of Unidirectionally Propagated Action Potentials in a Peripheral Nerve by Brief Stimuli", Science, 206(4424):1311-1312 (Dec. 14, 1979).
Van Wijk et al., "Gastric Emptying and Dyspeptic Symptoms in the Irritable Bowel Syndrome", Scand J Gastroenterol, 27(2):99-102 (1992).

(56) References Cited

OTHER PUBLICATIONS

Vassallo et al., "Colonic Tone and Motility in Patients with Irritable Bowel Syndrome", Mayo Clin Proc, 67(8):725-731 (Aug. 1992).

Waataja et al., "Effects of High-Frequency Alternating Current on Axonal Conduction Through the Vagus Nerve," Journal of Neural Engineering Neural Eng. 8(5):056013 (1741-1747), IOP Publishing Ltd, (Oct. 2011) online at stacks.iop.org.

Wilmer et al., "Ambulatory Gastrojejunal Manometry in Severe Motility-like Dyspepsia: Lack of Correlation between Dysmotility, Symptoms and Gastric Emptying", Gut, 42:235-242 (1998).

Wilson et al., "Intra-Abdominal Vagal Blocking Re3duces body Weight with Associated Reductions in Heart Rate and Without Adverse Effects on Electrocardiographic Parameters," Obesity Surgery: Including Laparoscopy and Allied Care, Program and Abstracts of the 13th World Congress of IFSO, Buenos Aires, Argentina, Sep. 24-27, 2008. An International Surgical Journal for Research and Treatment of Massive Obesity, 18(8):923 (Aug. 2008).

Wray et al., Reduced Calorie Intake and Weight Loss During Vagal Blocking in Subjects with Obesity-Related Type 2 Diabetes Mellitus, Obesity 2011 Abstract Supplement / Poster Abstracts—Monday, Oct. 3, 2011, Obesity, 19(Supp 1):S190 (Nov. 2011). www.obesityjournal.org.

Yoshinaga et al., "Cholecystokinin Acts as an Essential Factor in the Exacerbation of Pancreatic Bile Duct Ligation-Induced Rat Pancreatitis Model Under Non-Fasting Condition", Japanese J. Pharmacol, 84:44-50 (2000).

Zapater et al., "Do Muscarinic Receptors Play a Role in Acute Pancreatitis?", Clin. Drug Invest., 20(6):401-408 (2000).

Pacing Without Block

Pacing With Proximal and Distal Blocks

ELECTRODE BAND SYSTEM AND METHODS OF USING THE SYSTEM TO TREAT OBESITY

I. CROSS-REFERENCE TO RELATED APPLICATION

The present application is a continuation of U.S. patent application Ser. No. 13/758,223, filed Feb. 4, 2013, which is a continuation of U.S. patent application Ser. No. 13/178,221, filed Jul. 7, 2011, now U.S. Pat. No. 8,369,952, which is a continuation of U.S. patent application Ser. No. 11/656,121, filed Jan. 22, 2007, now U.S. Pat. No. 7,986,995, which is a continuation of U.S. patent application Ser. No. 10/752,944, filed Jan. 6, 2004, now U.S. Pat. No. 7,167,750, which is a continuation-in-part application of the following U.S. patent applications, all filed on Sep. 29, 2003: U.S. patent application Ser. No. 10/674,330, now U.S. Pat. No. 7,489,969; U.S. patent application Ser. No. 10/675,818, now abandoned, and U.S. patent application Ser. No. 10/674,324, now abandoned. The aforementioned patent applications are continuation-in-part applications of U.S. patent application Ser. No. 10/358,093, filed Feb. 3, 2003, now abandoned. The present application also claims priority to the aforesaid Serial No. 10/358,093.

II. BACKGROUND OF THE INVENTION

Field of the Invention

This invention pertains to treatments of disorders associated, at least in part, with neural activity. These may include, without limitation, gastrointestinal, pancreo-biliary, cardio-respiratory and central nervous system disorders (including neurological and psychiatric, psychological and panic disorders). More particularly, this invention pertains to treatment of such disorders through management of neural impulse stimulation and blocking.

Description of the Prior Art

A. Functional Gastrointestinal Disorders (FGIDs)

Functional Gastrointestinal Disorders (FGIDs) are a diagnostic grouping having diagnostic criteria based on symptomatology, because the pathophysiology of these diseases is multifactorial with some pathophysiologic mechanisms in common. FGIDs are thought to be due to altered autonomic nervous system balance and to be pathophysiological combinations of: (1) abnormal GI motility; (2) visceral hypersensitivity; and, (3) brain-gut interactions. Tougas, "The Autonomic Nervous System in Functional Bowel Disorders", Gut, Vol. 47 (Suppl IV), pp. iv78-iv80 (2000) and Drossman, "Rome II: A Multinational Consensus Document on Gastrointestinal Disorders—The Functional Gastrointestinal Disorders and the Rome II Process", Gut, Vol. 45 (Suppl II):II1-II5 (1999). The FGIDs of interest to the present invention are functional dyspepsia (dysmotility-like) and irritable bowel syndrome (IBS).

1. Functional Dyspepsia (Dysmotility-Like)

Functional dyspepsia (dysmotility-like), is diagnosed when a patient's symptoms, in the absence of other organic disease likely to explain the symptoms, include persistent or recurrent pain or discomfort centered in the upper abdomen that may be accompanied by upper abdominal fullness, early satiety, bloating or nausea. Talley et al., "Rome II: A Multinational Consensus Document on Gastrointestinal Disorders—Functional Gastroduodenal Disorders" Gut, Vol. 45 (Suppl II), pp. I37-II42 (1999).

A spectrum of dysmotilities has been documented in patients with functional dyspepsia. These include delayed gastric emptying of solids and liquids, reduced vagal tone, gastric dysrhythmias and impaired gastric accommodation. Furthermore, some studies have found good correlation between symptoms and indices of dysmotility, while others have not. Stanghellini V, et al., "Delayed Gastric Emptying of Solids in Patients with Functional Dyspepsia", Gastroenterol, (1996) 110:1036-1042. Undeland K A, et al., "Wide Gastric Antrum and Low Vagal Tone in Patients with Diabetes Mellitus Type 1 Compared to Patients with Functional Dyspepsia and Healthy Individuals", Dig Dis Sci, (1996) 41:9-16. Tack J, et al., "Role of Impaired Gastric Accommodation to a Meal in Functional Dyspepsia", Gastroenterol, (1998) 115:1346-1352. Wilmer A, et al., "Ambulatory Gastrojejunal Manometry in Severe Motility-like Dyspepsia: Lack of Correlation between Dysmotility, Symptoms and Gastric Emptying", Gut, (1998) 42:235-242. Tack J, et al., "Symptom Pattern and Gastric Emptying Rate Assessed by the Octanoic Acid Breath Test in Functional Dyspepsia" [abstract]. Gastroenterol, (1998) 114:A301. Cuomo R, et al., "Functional Dyspepsia Symptoms, Gastric Emptying and Satiety Provocation Test: Analysis of Relationships", Scand J Gastroenterol, (2001) 36:1030-1036. Sarnelli G, et al., "Symptoms Associated with Impaired Gastric Emptying of Solids and Liquids in Functional Dyspepsia", Am J Gastroenterol, (2003) 98:783-788.

2. Irritable Bowel Syndrome (IBS)

The second FGID of interest, IBS, is diagnosed when a patient's symptoms include persistent abdominal pain or discomfort, in the absence of other explanatory organic disease, along with at least two of the following: relief of pain with defecation, onset of symptoms associated with a change in frequency of stools and/or onset of symptoms associated with a change in appearance/form of stools. Thompson W G, et al., "Rome II: A Multinational Consensus Document on Gastrointestinal Disorders—Functional Bowel Disorders and Functional Abdominal Pain", Gut, (1999); 45(Suppl II):II43-II47.

In addition to colonic dysmotility, a number of other GI motility abnormalities have been identified, including delayed gastric emptying, gastroparesis, and small intestine motility abnormalities. Vassallo M J, et al., "Colonic Tone and Motility in Patients with Irritable Bowel Syndrome", Mayo Clin Proc, (1992); 67:725-731. Van Wijk H J, et al., "Gastric Emptying and Dyspeptic Symptoms in the Irritable Bowel Syndrome", Scand J Gastroenterol, (1992); 27:99-102. Evans P R, et al., "Gastroparesis and Small Bowel Dysmotility in Irritable Bowel Syndrome", Dig Dis Sci (1997); 42:2087-2093. Cann P A, et al. "Irritable Bowel Syndrome: Relationship of Disorders in the Transit of a Single Solid Meal to Symptoms Patterns", Gut, (1983); 24:405-411. Kellow J E, et al., "Dysmotility of the Small Intestine in Irritable Bowel Syndrome", Gut, (1988); 29:1236-1243. Evans P R, et al., "Jejunal Sensorimotor Dysfunction in Irritable Bowel Syndrome: Clinical and Psychosocial Features", Gastroenterol, (1996); 110:393-404. Schmidt T, et al., "Ambulatory 24-Hour Jejunal Motility in Diarrhea-Predominant Irritable Bowel Syndrome", J Gastroenterol, (1996); 31:581-589. Simren M, et al., "Abnormal Propagation Pattern of Duodenal Pressure Waves in the Irritable Bowel Syndrome (IBS)", Dig Dis Sci, (2000); 45:2151-2161.

A related finding is that patients with constipation-predominant IBS have evidence of decreased vagal tone, while diarrhea-predominant IBS is associated with evidence of increased sympathetic activity. Aggarwal A, et al., "Predominant Symptoms in Irritable Bowel Syndrome Correlate with Specific Autonomic Nervous system Abnormalities", *Gastroenterol*, (1994); 106:945-950.

There is no cure for IBS. Treatments include supportive palliative care (antidiarrheals, dietary modification and counseling).

A recently approved drug to treat selected patients with FGIDs is tegaserod maleate sold under the tradename "Zelnorm®" by Novartis Pharmaceuticals Corp., East Hanover, N.J., USA. The product literature on Zelnorm recognizes the enteric nervous system is a key element in treating IBS. The literature suggests Zelnorm® acts to enhance basal motor activity and to normalize impaired motility. Novartis product description, Zelnorm®, July 2002 (T2002-19). Zelnorm's approved use is limited to females with constipation-related IBS. It is for short-term use only.

B. Gastroparesis

The third disease indication discussed here, gastroparesis (or delayed gastric emptying) is associated with upper GI symptoms such as nausea, vomiting fullness, bloating and early satiety. Gastroparesis can be caused by many underlying conditions. The most important, because of chronicity and prevalence, are diabetes, idiopathic and post-surgical. Hornbuckle K, et al. "The Diagnosis and Work-Up of the Patient with Gastroparesis", *J Clin Gastroenterol*, (2000); 30:117-124. GI dysmotility in the form of delayed gastric emptying is, by definition, present in these patients.

In patients with Type 1 diabetes mellitus and delayed gastric emptying, there appears to be a relationship between delayed gastric emptying and low vagal tone. Merio R, et al., "Slow Gastric Emptying in Type 1 Diabetes: Relation to Autonomic and Peripheral Neuropathy, Blood Glucose, and Glycemic Control", *Diabetes Care*, (1997); 20:419-423. A related finding is that patients with Type 1 diabetes have low vagal tone in association with increased gastric antral size, possibly contributing to the dysmotility-associated symptoms seen in these patients. Undeland K A, et al., "Wide Gastric Antrum and Low Vagal Tone in Patients with Diabetes Mellitus Type 1 Compared to Patients with Functional Dyspepsia and Healthy Individuals", *Dig Dis Sci*, (1996); 41:9-16.

The current treatments for gastroparesis are far from satisfactory. They include supportive care, such as dietary modification, prokinetic drugs, and; when required, interventions such as intravenous fluids and placement of a nasogastric tube may be needed.

C. Gastroesophageal Reflux Disease (GERD)

The fourth indication, GERD, can be associated with a wide spectrum of symptoms, including dyspepsia, reflux of gastric contents into the mouth, dysphagia, persistent cough, refractory hyperreactive airway disease and even chronic serous otitis media. Sontag S J, et al., "Asthmatics with Gastroesophageal Reflux: Long Term Results of a Randomized Trial of Medical and Surgical Antireflux Therapies", *Am J Gastroenterol*, (2003); 98:987-999. Poelmans J, et al., "Prospective Study on the Incidence of Chronic Ear Complaints Related to Gastroesophageal Reflux and on the Outcome of Antireflux Therapy", *Ann Otol Rhinol Laryngol*, (2002); 111:933-938.

GERD is considered to be a chronic condition for which long-term medical therapy and/or surgical therapy is often deemed necessary, in significant part because esophageal adenocarcinoma is sometimes a consequence of GERD. DeVault K R, et al., "Updated Guidelines for the Diagnosis and Treatment of Gastroesophageal Reflux Disease", *Am J Gastroenterol*, (1999); 94:1434-1442. Lagergren J, et al., "Symptomatic Gastroesophageal Reflux as a Risk Factor for Esophageal Adenocarcinoma", *New Engl J Med*, (1999); 340:825-831.

The underlying pathophysiological mechanisms in GERD are considered to be transient lower esophageal relaxations (TLESRs) in the presence of either an inadequate pressure gradient between the stomach and the esophagus across the lower esophageal sphincter and/or low amplitude esophageal activity at times when gastric contents do reflux into the esophagus. In addition, gastric distention is thought to be associated with an increase in TLESRs. Mittal R K, et al., "Mechanism of Disease: The Esophagogastric Junction", *New Engl J Med*, (1997); 336:924-932. Scheffer R C, et al., "Elicitation of Transient Lower Oesophageal Sphincter Relaxations in Response to Gastric Distension", *Neurogastroenterol Motil*, (2002); 14:647-655.

GERD is generally considered to be the result of a motility disorder which permits the abnormal and prolonged exposure of the esophageal lumen to acidic gastric contents. Hunt, "The Relationship Between The Control Of pH And Healing And Symptom Relief In Gastro-Oesophageal Reflux Disease", *Ailment Pharmacol Ther.*, 9 (Suppl. 1) pp. 3-7 (1995). Many factors are believed to contribute to the onset of GERD. These include transient lower esophageal sphincter relaxations (as previously described), decreased LES resting tone, delayed stomach emptying and an ineffective esophageal clearance.

Certain drugs have had some effectiveness at controlling GERD but fail to treat underlying causes of the disease. Examples of such drugs are $H_2$-receptor antagonists (which control gastric acid secretion in the basal state) and proton pump inhibitors (which control meal-stimulated acid secretion). Hunt, id. Both classes of drugs can raise intragastric pH to or about 4 for varying durations. Hunt, supra.

Surgery treatments are also employed for the treatment of GERD and include techniques for bulking the lower esophageal sphincter such as fundoplication and techniques described in U.S. Pat. No. 6,098,629 Johnson et al, Aug. 8, 2000. Other surgical techniques include placement of pacemakers for stimulating muscle contractions in the esophageal sphincter, the stomach muscles or in the pyloric valve. U.S. Pat. No. 6,104,955 to Bourgeois, U.S. Pat. No. 5,861, 014 to Familoni.

A summary of GERD treatments can be found in DeVault, et al., "Updated Guidelines for the Diagnosis and Treatment of Gastroesophageal Reflux Disease", Amer. J. of Gastroenterology, Vol. 94, No. 6, pp. 1434-1442 (1999).

Notwithstanding multiple attempts at various types of treatment, GERD continues to be a serious disease proving to be difficult to treat by any of the foregoing prior art techniques. In view of the foregoing and notwithstanding various efforts exemplified in the prior art, there remains a need for an effective treatment for GERD. It is an object of the present invention to provide a novel treatment and novel apparatus for the treatment of GERD.

D. Electrical Stimulation to Treat GI Disorders

Treatment of gastrointestinal diseases through nerve stimulation have been suggested. For example, U.S. Pat. No. 6,238,423 to Bardy dated May 29, 2001 describes a constipation treatment involving electrical stimulation of the muscles or related nerves of the gut. U.S. Pat. No. 6,571,127 to Ben-Haim et al. dated May 27, 2003 describes increasing motility by applying an electrical field to the GI tract. U.S. Pat. No. 5,540,730 to Terry, Jr. et al., dated Jul. 30, 1996 describes a motility treatment involving vagal stimulation to alter GI contractions in response to a sense condition indicative of need for treatment. The '730 patent also uses a definition of dysmotility more restrictive than in the present application. In the '730 patent, dysmotility is described as hyper- or hypo-contractility. In the present application, dysmotility is a broader concept to refer to all abnormalities of gastric emptying or bowel transfer regardless of cause. U.S. Pat. No. 6,610,713 to Tracey dated Aug. 26, 2003 describes inhibiting release of a proinflammatory cytokine by treating a cell with a cholinergic agonist by stimulating efferent vagus nerve activity to inhibit the inflammatory cytokine cascade.

A substantial body of literature is developed on nerve stimulation. For example, in Dapoigny et al., "Vagal influence on colonic motor activity in conscious nonhuman primates", *Am. J. Physiol.*, 262:G231-G236 (1992), vagal influence on colonic motor activity was investigated in conscious monkeys. To block antidromic interference, the vagus was blocked via vagal cooling and a vagal stimulation electrode was implanted distal to the vagal block. It was noted that vagal efferent stimulation increased contractile frequency and that the vagus has either a direct or indirect influence on fasting and fed colonic motor activity throughout the colon, and that a non-adrenergic, noncholinergic inhibitory pathway is under vagal control.

Colonic and gastric stimulation are also described in a number of articles associated with M. P. Mintchev. These include: Mintchev, et al., "Electrogastrographic impact of multi-site functional gastric electrical stimulation", *J. of Medical Eng. & Tech.*, Vol. 23, No. 1, pp. 5-9 (1999); Rashev, et al., "Three-dimensional static parametric modeling of phasic colonic contractions for the purpose of microprocessor-controlled functional stimulation", *J. of Medical Eng. & Tech.*, Vol. 25, No. 3 pp. 85-96 (2001); Lin et al., "Hardware-software co-design of portable functional gastrointestinal stimulator system", *J. of Medical Eng. & Tech.*, Vol. 27, No. 4 pp. 164-177 (2003); Amaris et al., "Microprocessor controlled movement of solid colonic content using sequential neural electrical stimulation", *Gut*, 50: pp 475-479 (2002) and Rashev et al., "Microprocessor-Controlled Colonic Peristalsis", *Digestive Diseases and Sciences*, Vol. 47, No. 5, pp. 1034-1048 (2002).

The foregoing references describe nerve stimulation to stimulate muscular contraction in the GI tract. As will be more fully discussed, the present invention utilizes vagal stimulation to improve vagal tone (similar in concept to improving cardiac electrical tone through cardiac pacing) and/or to treat GI disorders by altering the nature of duodenum contents by stimulation pancreatic and biliary output. The invention is also applicable to treating other diseases such as neuropsychiatric disorders.

Vagal tone has been shown to be associated with dyspepsia. Hjelland, et al., "Vagal tone and meal-induced abdominal symptoms in healthy subjects", Digestion, 65: 172-176 (2002). Also, Hausken, et al., "Low Vagal Tone and Antral Dysmotility in Patients with Functional Dyspepsia", *Psychosomatic Medicine*, 55:12-22 (1993). Also, decreased vagal tone has been associated with irritable bowel syndrome. Heitkemper, et al., "Evidence for Automatic Nervous System Imbalance in Women with Irritable Bowel Syndrome", *Digestive Diseases and Sciences*, Vol. 43, No. 9, pp. 2093-2098 (1998).

Also, as will be discussed, the present invention includes, in several embodiments, a blocking of a nerve (such as the vagal nerve) to avoid antidromic influences during stimulation. Cryogenic nerve blocking of the vagus is described in Dapoigny et al., "Vagal influence on colonic motor activity in conscious nonhuman primates", *Am. J. Physiol.*, 262: G231-G236 (1992). Electrically induced nerve blocking is described in Van Den Honert, et al., "Generation of Unidirectionally Propagated Action Potentials in a Peripheral Nerve by Brief Stimuli", *Science*, Vol. 206, pp. 1311-1312. An electrical nerve block is described in Solomonow, et al., "Control of Muscle Contractile Force through Indirect High-Frequency Stimulation", *Am. J. of Physical Medicine*, Vol. 62, No. 2, pp. 71-82 (1983) and Petrofsky, et al., "Impact of Recruitment Order on Electrode Design for Neural Prosthetics of Skeletal Muscle", *Am. J. of Physical Medicine*, Vol. 60, No. 5, pp. 243-253 (1981). A neural prosthesis with an electrical nerve block is also described in U.S. Patent Application Publication No. US 2002/0055779 A1 to Andrews published May 9, 2002. A cryogenic vagal block and resulting effect on gastric emptying are described in Paterson C A, et al., "Determinants of Occurrence and Volume of Transpyloric Flow During Gastric Emptying of Liquids in Dogs: Importance of Vagal Input", *Dig Dis Sci*, (2000); 45:1509-1516.

III. SUMMARY OF THE INVENTION

A method and apparatus for treating at least one of a plurality of disorders of a patient are disclosed where the disorders are characterized at least in part by vagal activity innervating at least one of a plurality of organs of the patient at an innervation site. The method includes positioning an electrode on a vagus nerve. An electrical signal is applied to the electrode to modulate vagal activity by an amount selected to treat the disorder. In some embodiments, the disorder is bulimia. The signal may be a blocking or a stimulation signal. In some embodiments, the signal is selected to, at least in part, downregulate neural activity on the vagus nerve.

IV. BRIEF DESCRIPTION OF THE DRAWINGS

V. DESCRIPTION OF THE PREFERRED EMBODIMENT

With reference now to the various drawing figures in which identical elements are numbered identically throughout, a description of the preferred embodiment of the present invention will now be described.

A. Invention of Parent Application

Figure 1:
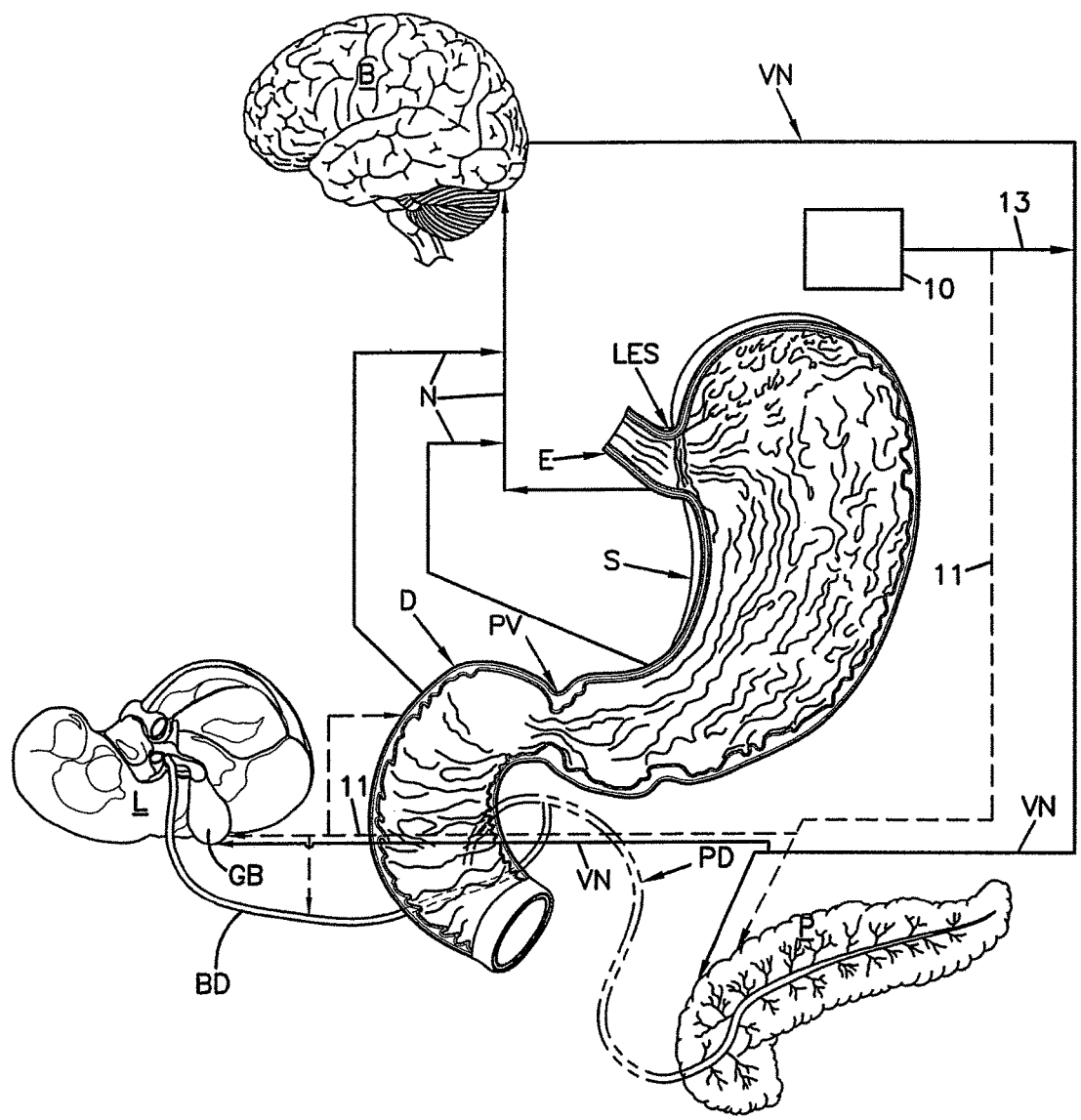
FIG. 1 is a schematic representation of a gastric-emptying feedback loop with a patient-controlled stimulator for stimulating an organ of the loop.
Figure 2:
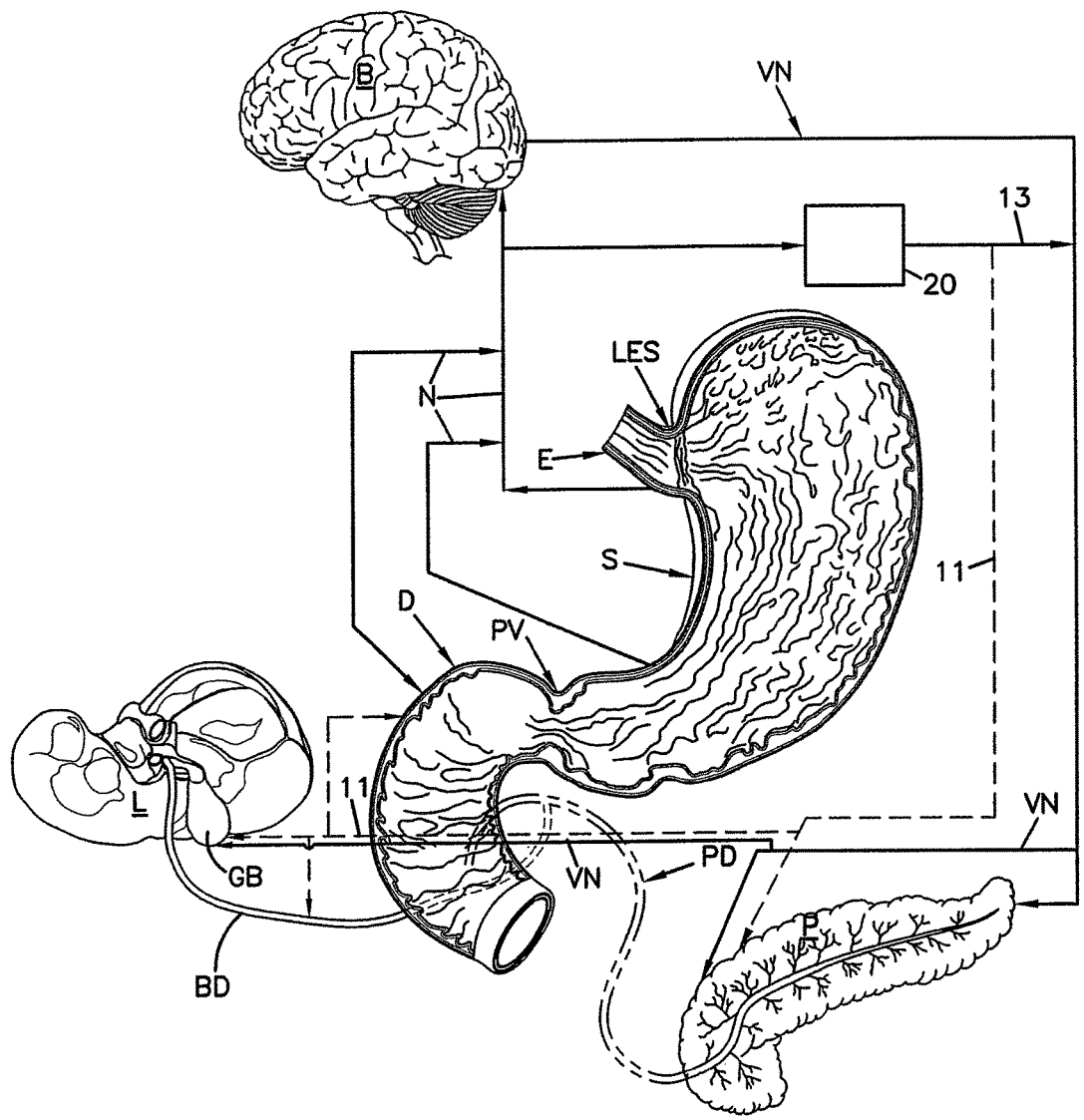
FIG. 2 is a view similar to FIG. 1 with an automatic controller replacing the patient-controller of FIG. 1 and with feedback circuits to the automatic controller schematically represented.

FIGS. 1 and 2 and the description which follow are from the aforementioned U.S. patent application Ser. No. 10/358,093 filed Feb. 3, 2003 and entitled "Method and Apparatus for Treatment of Gastroesophageal Disease (GERD)".

With initial reference to FIG. 1, a gastric emptying feedback loop is shown schematically for ease of illustration. The feedback loop illustrates a patient's stomach S which is provided with food from the esophagus E. A lower esophageal sphincter LES is shown positioned between the esophagus E and the stomach S. The lower esophageal sphincter normally provides control of reflux of stomach contents into the esophagus E.

On a proximal or lower end of the stomach S the stomach discharges into the superior duodenum D which is an upper portion of the intestines. The superior duodenum D and the stomach S are separated by a pyloric valve PV which opens to permit gastric emptying from the stomach into the duodenum D.

Also schematically illustrated in FIG. 1 are nerve paths N providing signal flow paths from both the superior duodenum D and the stomach S to the brain B. An efferent Vagal nerve VN connects the brain B to the pancreas P of the patient. A conduit (pancreatic duct PD) extends from the pancreas P and discharges into the superior duodenum D.

The presence of food contents within the duodenum D (such contents being referred to as "chyme") may prevent passage of gastric content of the stomach S past the pyloric valve PV into the duodenum D. As long as such gastric contents cannot be passed into the duodenum D, such contents can be forced retrograde past the lower esophageal sphincter LES and into the esophagus E creating the symptoms and discomfort of GERD. The contents discharging from the stomach S into the duodenum D are acidic (and high osmolality) and reside in the duodenum D until pH is elevated (close to a neutral pH of 6-7) and osmolality is normalized.

The elevation of pH and reduction of osmolality of chyme in the duodenum D results from exocrine secretion being administered from the pancreas P and from bile from the liver into the duodenum D. This raises the pH and lowers the osmolality of the duodenum D content permitting discharge from the duodenum D and thereby permitting gastric emptying across the pyloric valve PV.

According to the present invention gastroesophageal reflux disease (GERD) results from a derangement of the feedback loops involved in upper GI digestion and motility control. This problem encompasses receptors and reflexes that regulate the propulsive contractions of the stomach, upper duodenum and biliary tree and the secretions of the exocrine pancreas. The interaction of these receptors and reflexes control gastric emptying (by coordinating gastric propulsive contractions and sphincter [primarily pyloric] tone) and regulate the pH and osmolality of the chyme in the duodenum. This chemo-regulation is mediated through control of bile delivery and stimulation of secretion by the exocrine pancreas of fluid delivered to the superior duodenum. Chey et al., "Neural Hormonal Regulation of Exocrine Pancreatic Secretion", Pancreatology, pp. 320-335 (2001).

Normally, ingestate delivered to the stomach is mixed by low intensity gastric mixing contractions with the enzymatic, ionic, including hydrogen ion (H+), and water secretions of the glands of the stomach. When the material is adequately reduced in size and is a smooth consistency, the fluid, now called chyme, is delivered to the ampulla of the small intestine by the much stronger propulsive, or emptying, contractions of the stomach coupled with transitory relaxation of the pyloric sphincter. This material is at a very low pH (about 2) and high osmolality, which activates receptors, including those for $H^+$ and osmotic pressure, which are abundant in the wall of the ampulla. This receptor activation initiates the series of reflexes that cause pancreatic exocrine secretion to be delivered into the superior duodenum and ampulla. This fluid contains digestive enzymes, water and buffering compounds to raise the pH, and reduce the osmolality, of the chyme.

Once a neutral pH and physiological osmolality are achieved, then propulsive contractions in the superior duodenum move the chyme out of the superior portion into the length of the duodenum; at which point the stretch and baro-receptors in the ampulla allow the pyloric sphincter to relax and another bolus of gastric contents is delivered into the ampulla by the peristaltic gastric emptying contractions. This material, at a very low pH (less than 2), activates hydrogen ion ($H^+$) on receptors of the ampulla (upper most portion of the duodenum) causing the pancreatic fluids to be delivered to the material in the ampulla restarting the cycle as described above. Chapter 3, "The Stomach", Gastrointestinal System, $2^{nd}$ Ed., M. S. Long editor, Mosby Publisher, London (2002).

If the control system is down regulated by, for example, by increased pH of gastric contents entering the ampulla, feedback may thereby be reduced from the $H^+$ receptors in the duodenum that stimulate pancreatic exocrine secretion and bile delivery to the duodenum, then movement of chyme from the superior duodenum is delayed, causing delay of gastric emptying. Mabayo, et al., "Inhibition of Food Passage by Osmeprazole in the Chicken", European J. of Pharmacology, pp. 161-165 (1995).

In GERD, this reflex is inhibited in such a way that the stomach empties more slowly so that the gastric emptying contractions force gastric contents to flow retrograde into the esophagus. This is a result of the situation in which the gastric emptying contractions are vigorous but must operate against a contracted pyloric sphincter. These vigorous peristaltic contractions eventually begin to force gastric contents to flow retrograde into the esophagus because of the inherent imbalance between a very strong pyloric sphincter and a much weaker gastroesophageal sphincter. The delay in gastric emptying is directly related to a slow down in the transport of chyme out of the ampulla and superior duodenum. The drugs used to treat this disease raise pH further dampening the hydrogen-receptor-pancreatic secretion loop, further delaying gastric emptying. Benini, "Gastric Emptying and Dyspeptic Symptoms in Patients with Gastroesophageal Reflux", Amer. J. of Gastroenterology, pp. 1351-1354 (1996).

The present invention is directed towards reestablishing the link between gastric emptying and pancreatic secretion delivery, thereby addressing the main pathology of this disease by shortening chyme residence time in the superior duodenum so that intestinal contents move into the distal digestive tract in a more normal manner. According to a first embodiment, this is done by stimulating the H+ ion receptors or by stimulation of the pancreas directly or via its para-sympathetic innervation (pre-ganglionic Vagal nerves). Stimulation of pancreatic exocrine secretion has been shown by direct stimulation of the thoracic vagus nerves in dogs. Kaminski et al., "The Effect of Electrical Vagal Stimulation on Canine Pancreatic Exocrine Function", Surgery, pp. 545-552 (1975). This results in a more rapid (normal) neutralization of chyme in the ampulla, allowing it move down the duodenum more quickly so that gastric emptying is returned to a more normal pace.

Acidity (pH) can be assessed by measuring bicarbonate. It will be understood that references to —H includes such indirect measurements. Also, effects of the therapy described herein can be assessed and/or controlled by measuring an indication of pancreatic exocrine secretion or bile (e.g., $HCO_3^-$).

An alternative embodiment uses gastrocopic delivery of a paralyzing agent (e.g. botulism toxin) to the pyloric valve along with use of H2 antagonists or PPI's to manage the acidity of the chyme reaching the duodenum.

As an additional alternative to pancreatic stimulation, the gall bladder can be stimulated to encourage bile movement into the duodenum. Shown schematically in the figures, the gall bladder GB resides below the liver L. The gall bladder is connected to the small intestine (specifically the duodenum D) via a bile duct BD. The bile duct BD can discharge directly into the duodenum D or via the pancreatic duct PD as shown. The bile can normalize the chyme to accelerate duodenal emptying. Bile consists of bile acids (detergents that emulsify lipids), cholesterol, phospholipids, electrolytes such as ($Na^+$, $K^+$, $Ca^{+2}$, $Cl^-$, $HCO_3^-$) and $H_2O$. Chapter 4, "The Liver and Biliary Tract", Gastrointestinal System, $2^{nd}$ Ed., M. S. Long editor, Mosby Publisher, London (2002). The gall bladder GB or bile duct can be stimulated indirectly via stimulation of the vagal nerve VN or directly stimulated by an electrode 11 (shown in phantom lines).

As illustrated in the figures, an electrical stimulator 10, 20 which may be implanted is provided which alternatively may be directly connected to the Vagal nerve VN or the pancreas P to stimulate the pancreas directly or indirectly to excrete exocrine into the duodenum D (or more distally into the small intestine—e.g., into the jejunum) and increase the pH of chyme in the duodenum D as described. Alternatively, the same can be done to promote bile release. The frequency may be varied to maximize the response and selectively stimulate exocrine instead of endocrine secretions. Rösch et al., "Frequency-Dependent Secretion of Pancreatic Amylase, Lipase, Trypsin, and Chymotrypsin During Vagal Stimulation in Rats", Pancreas, pp. 499-506 (1990). See, also, Berthoud et al., "Characteristics of Gastric and Pancreatic Reponses to Vagal Stimulation with Varied Frequencies: Evidence for Different Fiber Calibers?", J. Auto. Nervous Sys., pp. 77-84 (1987) (showed frequency-response relationship with insulin, i.e., significantly less insulin was released at lower frequencies—2 Hz v. 8 Hz—also, frequency-response curves evidenced distinctly different profiles for gastric, pancreatic and cardiovascular responses.) Slight insulin release can maximize pancreatic exocrine secretion. Chey et al., "Neural Hormonal Regulation of Exocrine Pancreatic Secretion", Pancreatology, pp. 320-335 (2001).

With a patient control stimulation as shown in FIG. 1, the patient may activate the stimulator 10 by remote transmitter to stimulate an electrical charge either after eating (e.g., about 60 to 90 minutes after eating) or on onset of GERD symptoms. It will be appreciated that there are a wide variety of nerve stimulators and organ stimulators available for implantation and are commercially available and which include connectors for connecting directly to nerves.

FIG. 2 illustrates an additional embodiment where the patient activated loop is replaced with an automatic loop having a programmable stimulator 20 which receives as an input signals from sensors in the duodenum to measure pH, osmolality or strain (e.g., from baro-sensors) on the duodenum indicating filling or may measure acidity in the esophagus or strain on the lower esophageal sphincter LES or stomach S all of which may be provided to the implantable controller 20 which can be provided with desirable software to process the incoming signals and generate a stimulating signal to either the vagal nerve, the pancreas P or the duodenum D (or jejunum) directly in response to such received signals. It will be appreciated that stimulators and controllers are well within the skill of the art. U.S. Pat. No. 5,540,730 teaches a neurostimulator to stimulate a vagus nerve to treat a motility disorder. U.S. Pat. No. 5,292,344 teaches gastrointestinal sensors, including pH sensors.

B. Application of Parent Application to Treatments Other than GERD

In addition to treatment of GERD, the foregoing invention is applicable to treatment of a plurality of GI diseases associated with delayed gastric emptying or altered autonomic activity. These include functional gastrointestinal disorders and gastroparesis. Furthermore, applicants have determined that duodenal content impacts a plurality of motility disorders throughout the bowels and can diseases associated with dysmotility (e.g., irritable bowel syndrome). Accordingly it is an object of the present invention to use the teachings of the aforementioned parent application to treat GI disorders associated with delayed gastric emptying and abnormal intestinal transport.

C. Additional Disclosure of the Present Application

1. Enteric Innervation

Figure 3:
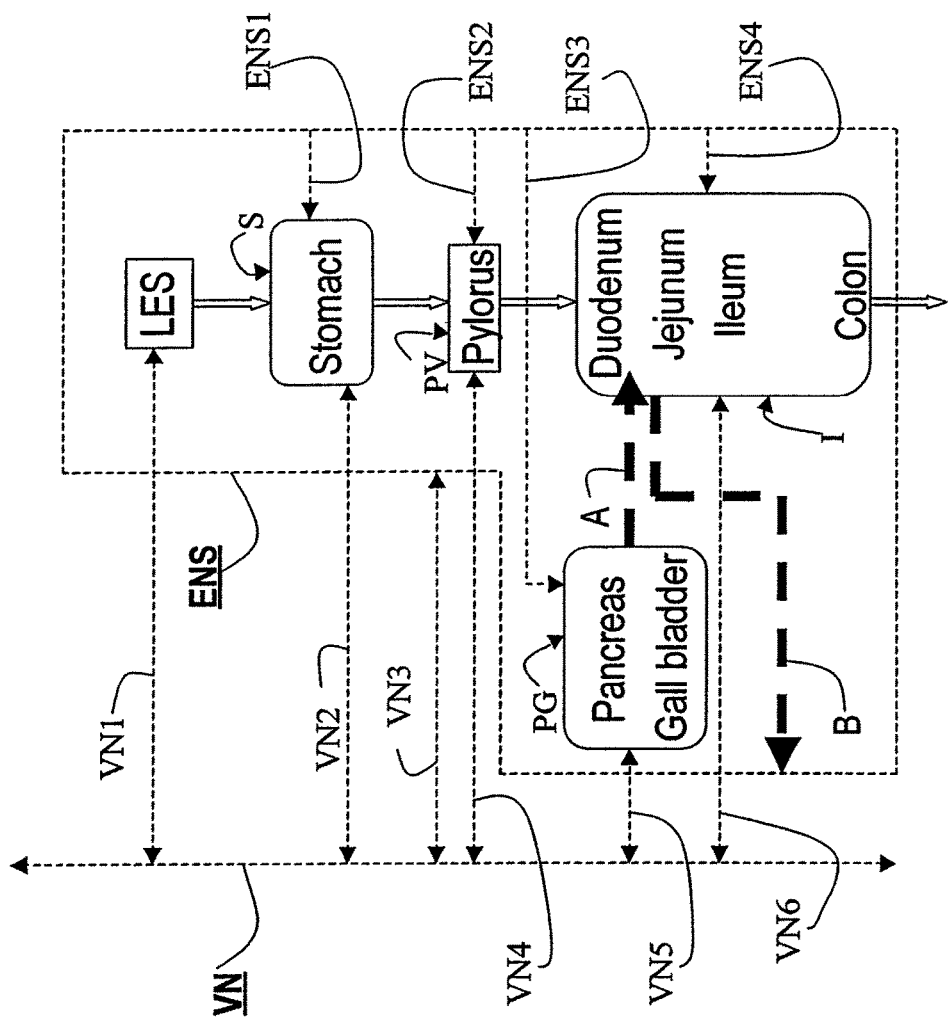
FIG. 3 is a schematic illustration of an alimentary tract (GI tract plus non-GI organs such as the pancreas and liver) and its relation to vagal and enteric innervation.

FIG. 3 is a schematic illustration of an alimentary tract (GI tract plus non-GI organs such as the pancreas and ball bladder, collectively labeled PG) and its relation to vagal and enteric innervation. The lower esophageal sphincter (LES) acts as a gate to pass food into the stomach S and, assuming adequate function of all components, prevent reflux. The pylorus PV controls passage of chyme from the stomach S into the intestines I (collectively shown in the figures and including the large intestine or colon and the small intestine including the duodenum, jejunum and ileum).

The biochemistry of the contents of the intestines I is influenced by the pancreas P and gall bladder PG which discharge into the duodenum. This discharge is illustrated by dotted arrow A.

The vagus nerve VN transmits signals to the stomach S, pylorus PV, pancreas and gall bladder PG directly. Originating in the brain, there is a common vagus nerve VN in the region of the diaphragm (not shown). In the region of the diaphragm, the vagus VN separates into anterior and posterior components with both acting to innervate the GI tract. In FIGS. 3, 5-8, the anterior and posterior vagus nerves are not shown separately. Instead, the vagus nerve VN is shown schematically to include both anterior and posterior nerves.

The vagus nerve VN contains both afferent and efferent components sending signals away from and to, respectively, its innervated organs.

In addition to influence from the vagus nerve VN, the GI and alimentary tracts are greatly influenced by the enteric nervous system ENS. The enteric nervous system ENS is an interconnected network of nerves, receptors and actuators throughout the GI tract. There are many millions of nerve endings of the enteric nervous system ENS in the tissues of the GI organs. For ease of illustration, the enteric nervous system ENS is illustrated as a line enveloping the organs innervated by the enteric nervous system ENS.

The vagus nerve VN innervates, at least in part, the enteric nervous system ENS (schematically illustrated by vagal trunk VN3 which represents many vagus-ENS innervation throughout the cut). Also, receptors in the intestines I connect to the enteric nervous system ENS. Arrow B in the figures illustrates the influence of duodenal contents on the enteric nervous system ENS as a feedback to the secretion function of the pancreas, liver and gall bladder. Specifically, receptors in the intestine I respond the biochemistry of the intestine contents (which are chemically modulated by the pancreao-biliary output of Arrow A). This biochemistry includes pH and osmolality.

In the figures, vagal trunks VN1, VN2, VN4 and VN6 illustrate schematically the direct vagal innervation of the GI organs of the LES, stomach S, pylorus PV and intestines I. Trunk VN3 illustrates direct communication between the vagus VN and the ENS. Trunk VN5 illustrates direct vagal innervation of the pancreas and gall bladder. Enteric nerves ENS1-ENS4 represent the multitude of enteric nerves in the stomach S, pylorus PV, pancreas and gall bladder PG and intestines I.

While communicating with the vagus nerve VN, the enteric nervous system ENS can act independently of the vagus and the central nervous system. For example, in patients with a severed vagus nerve (vagotomy—an historical procedure for treating ulcers), the enteric nervous system can operate the gut. Most enteric nerve cells are not directly innervated by the vagus. Gershon, "The Second Brain", Harper Collins Publishers, Inc, New York, N.Y. p. 19 (1998).

In FIG. 3, the vagus VN and its trunks (illustrated as VN1-VN6) and the enteric nervous system ENS are shown in phantom lines to illustrate reduced vagal and enteric nerve tone (i.e., sub-optimal nerve transmission levels). Reduced vagal and enteric tone contribute directly to the ineffectiveness of the GI organs as well as indirectly (through reduced pancreatic/biliary output). The reduced pancreatic/biliary output is illustrated by the dotted presentation of arrow A. As previously discussed, the vagus can be stimulated to stimulate pancreatic or biliary output. Therefore, the reduced output of arrow A results in a reduced feedback illustrated by the dotted presentation of arrow B.

2. Enteric Rhythm Management (ERM)

Figure 4:
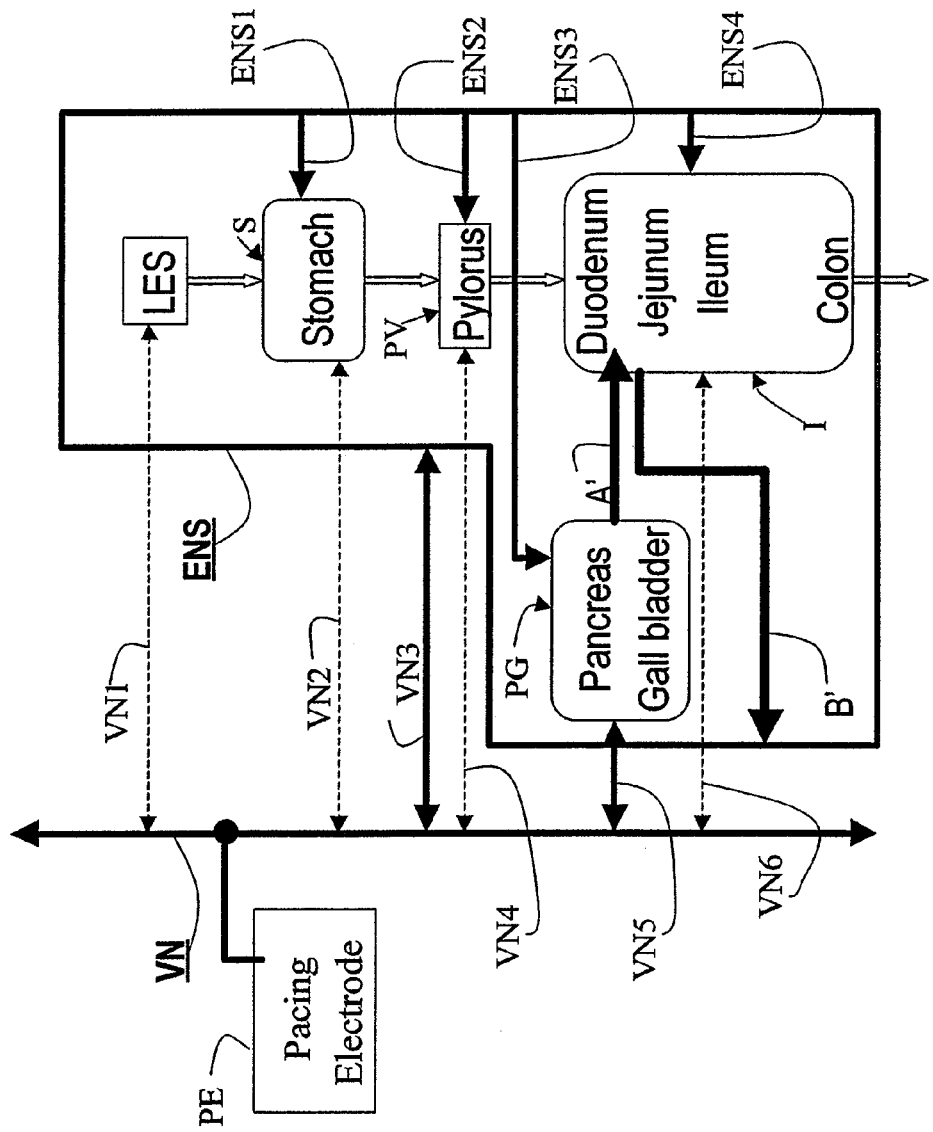
FIG. 4 is the view of FIG. 3 showing the application of a pacing electrode according to an embodiment of the present invention.

The benefits of the present invention are illustrated in FIG. 4 where a stimulating or pacing electrode PE is applied to the vagus VN. While only one electrode is shown in FIG. 4, separate electrodes could be applied to both the anterior and posterior vagus nerves (or to the common vagus or vagal branches). In a preferred embodiment, the electrode PE is placed a few centimeters below the diaphragm and proximal to stomach and pancreo/biliary innervation. While this placement is presently preferred for ease of surgical access, other placement locations may be used.

By pacing the vagus through the pacing electrode, vagal tone is optimized by either up- or down-regulation. With reference to the parasympathetic and enteric nervous systems, "tone" refers to basal activity of a nerve or nervous system facilitating appropriate physiologic response to a patient's internal environment. For example, low vagal tone implies a reduction in vagus nerve activity resulting in decreased response of the alimentary tract to ingested food. As used in the present application, "pacing" is not limited to mean timed events coordinated with specifically timed physiologic events. Instead, pacing means any electrical stimulation of a nerve trunk to induce bi-directional propagation of nervous impulses in the stimulated nerve.

The operating effectiveness of the vagus is enhanced so that local physiological signals generated in the enteric nervous system (or sent to the brain from the organs) are more appropriately responded to within the alimentary tract. Due to its innervation of the enteric nervous system, pacing of the vagus enhances the functional tone of the enteric nervous system. By enhancing the functional tone it will be noted that the stimulation pacing is elevating the degree of functionality of the vagus and enteric nerves. In this context, "pacing" is not meant to mean timed pulsed coordinated with muscular contractions or synchronized with other invents. Pacing means elevating the activity level of the nerves.

Tonal enhancement of the vagus and enteric nerves is illustrated by the solid lines for the nerves VN, ENS in FIG. 4. Vagal trunk VN5 is in solid line to illustrate enhanced tone of the many vagal nerve components communicating with the enteric nervous system ENS. Direct vagal innervation of the LES, stomach S, pylorus PV and intestines I remains shown as low tone indicated by phantom lines VN1, VN2, VN4, VN6. The tonal pacing described herein is not intended to trigger or drive the muscular contractility of these organs. The stimulation is not intended to be timed to trigger contractility and is not provided with an energy level sufficient to drive peristaltic contractions. Instead, these functions remain controlled by the central and enteric nerves systems. The enhanced nerve tone provided by the present invention permits these functions to occur.

Pacing to enhance vagal tone is not initiated in response to any senses event (or in anticipation of an immediate need to GI activity). Instead, the pacing can be done intermittently over the day to provide an enhanced level of operating functionality to the vagus. By way of non-limiting example, the stimulation pacing can be done during awake hours. For example, every ten minutes, pacing signals can be sent to the pacing electrodes. The pacing signals have a duration of 30 seconds with a current of 4 mA, a frequency of 12 Hz and an impulse duration of 2 msec. These parameters are representative only. A wide range of signal parameters may be used to stimulate the vagus nerve. Examples of these are recited in the afore-referenced literature.

As will be further discussed, the present invention permits ERM to be uniquely designed and modified by an attending physician to meet the specific needs of individual patients. For example, pacing can be limited to discrete intervals in the morning, afternoon and evening with the patient free to coordinate meals around these events.

In addition to enhancing vagal and enteric tone directly, the pacing also enhances the pancreatic and biliary output for the reasons discussed above. Namely, while ERM does not drive muscular events over nerve trunks VN1, VN2, VN4, VN6, the enhanced tone stimulates pancreo-biliary output over trunk VN5 (illustrated by the solid line of VN5 in FIG. 4). This enhanced output is illustrated as solid arrow A' in FIG. 4. As a consequence there is a greater feedback to the intestinal receptors as illustrated by solid arrow B' in FIG. 4. This enhanced biochemistry feedback further enhances the tone of the enteric nervous system ENS.

3. Implantable Pacing Circuit

Figure 5:
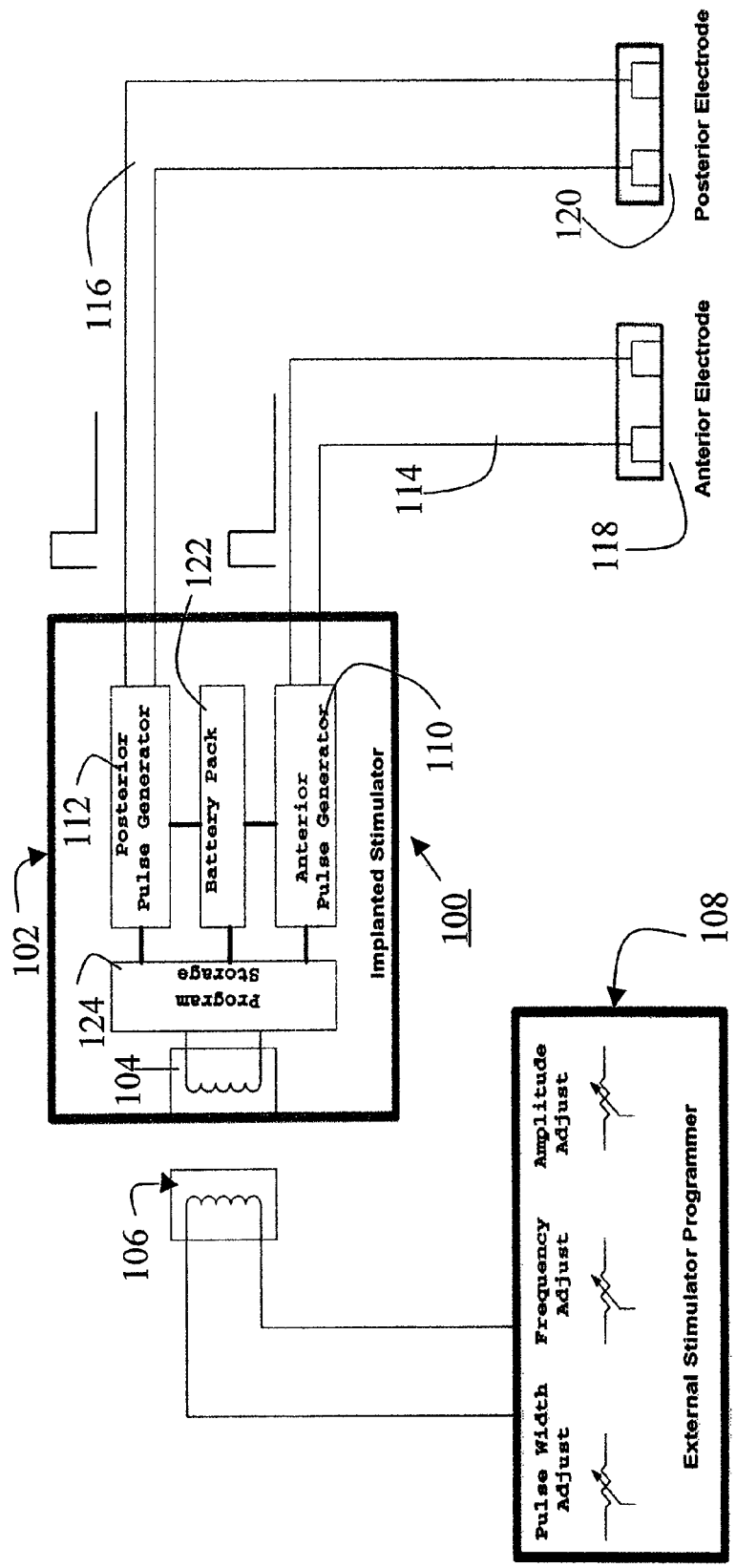
FIG. 5 is a schematic representation of pacing system.

A representative pacing circuit 100 is schematically shown in FIG. 5. Similar to cardiac pacing devices, an implantable controller 102 contains an induction coil 104 for inductive electrical coupling to a coil 106 of an external controller 108. The implantable controller 102 includes anterior and posterior pulse generators 110, 112 electrically connected through conductors 114, 116 to anterior and posterior pacing electrodes 118, 120 for attachment to anterior and posterior trunks, respectively, of the vagus nerve VN. The implantable controller 102 also includes a battery 122 and a CPU 124 which includes program storage and memory. The timing and parameters of the pulse at the electrodes 118, 120 can be adjusted by inductively coupling the external controller 108 to the implantable controller 102 and inputting pacing parameters (e.g., pulse width, frequency and amplitude).

While a fully implantable controller 102 is desirable, it is not necessary. For example, the electrodes 118, 120 can be implanted connected to a receiving antenna placed near the body surface. The control circuits (i.e., the elements 124, 110, 112 and 108) can be housed in an external pack worn by the patient with a transmitting antenna held in place on the skin over the area of the implanted receiving antenna. Such a design is forward-compatible in that the implanted electrodes can be later substituted with the implantable controller 102 at a later surgery if desired.

Although not shown in FIG. 5, the controller 102 can also include circuits generating nerve conduction block signals (as will be described) which connect to electrodes which may be positioned on a nerve proximally, distally (or both) of the electrodes 118, 120.

4. Nerve Conduction Block

Figure 6:
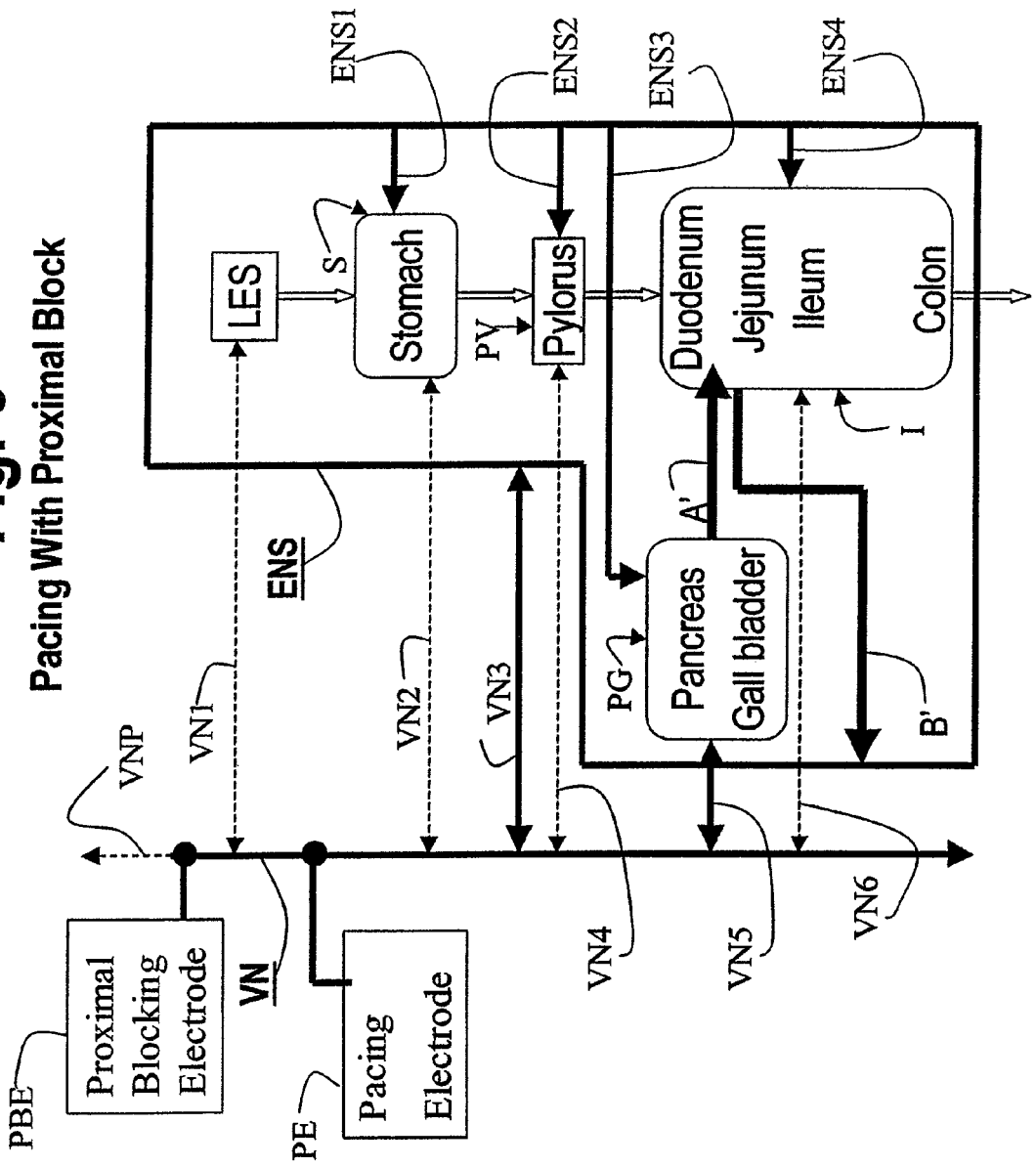
FIG. 6 is the view of FIG. 4 showing the application of a nerve conduction block electrode proximal to the pacing electrode.

FIG. 6 shows an alternative embodiment using a nerve conduction blocking electrode PBE proximal to the pacing electrode for providing a conduction block. A nerve block is, functionally speaking, a reversible vagotomy. Namely, application of the block at least partially prevents nerve transmission across the site of the block. Removal of the block restores normal nerve activity at the site. A block is any localized imposition of conditions that at least partially diminish transmission of impulses.

The vagal block may be desirable in some patients since unblocked pacing may result in afferent vagal and antidromic efferent signals having undesired effect on organs innervated by the vagus proximal to the GI tract (e.g., undesirable cardiac response). Further, the afferent signals of the pacing electrode PE can result in a central nervous system response that tends to offset the benefits of the pacing electrode on the ENS and pancreo/biliary function, thereby reducing the GI and enteric rhythm management effectiveness of vagal pacing.

The block may be intermittent and applied only when the vagus is paced by the pacing electrode PE. The preferred nerve conduction block is an electronic block created by a signal at the vagus by an electrode PBE controlled by the implantable controller (such as controller 102 or an external controller). The nerve conduction block can be any reversible block. For example, cryogenics (either chemically or electronically induced) or drug blocks can be used. An electronic cryogenic block may be a Peltier solid-state device which cools in response to a current and may be electrically controlled to regulate cooling. Drug blocks may include a pump-controlled subcutaneous drug delivery.

With such an electrode conduction block, the block parameters (signal type and timing) can be altered by a controller and can be coordinated with the pacing signals to block only during pacing. A representative blocking signal is a 500 Hz signal with other parameters (e.g., timing and current) matched to be the same as the pacing signal). While an alternating current blocking signal is described, a direct current (e.g., −70 mV DC) could be used. The foregoing specific examples of blocking signals are representative only. Other examples and ranges of blocking signals are described in the afore-mentioned literature (all incorporated herein by reference). As will be more fully described, the present invention gives a physician great latitude in selected pacing and blocking parameters for individual patients.

Similar to FIG. 4, the vagus VN and enteric nervous system ENS in FIG. 6 distal to the block PBE are shown in solid lines to illustrate enhanced tone (except for the direct innervation VN1, VN2, VN4, VN6 to the GI tract organs). Similarly, arrows A', B' are shown in solid lines to illustrate the enhanced pancreo-biliary output and resultant enhanced feedback stimulation to the enteric nervous system ENS. The proximal vagus nerve segment VNP proximal to the block PBE is shown in phantom lines to illustrate it is not stimulated by the pacing electrode PE while the blocking electrode PBE is activated.

5. Proximal and Distal Blocking

Figure 7:
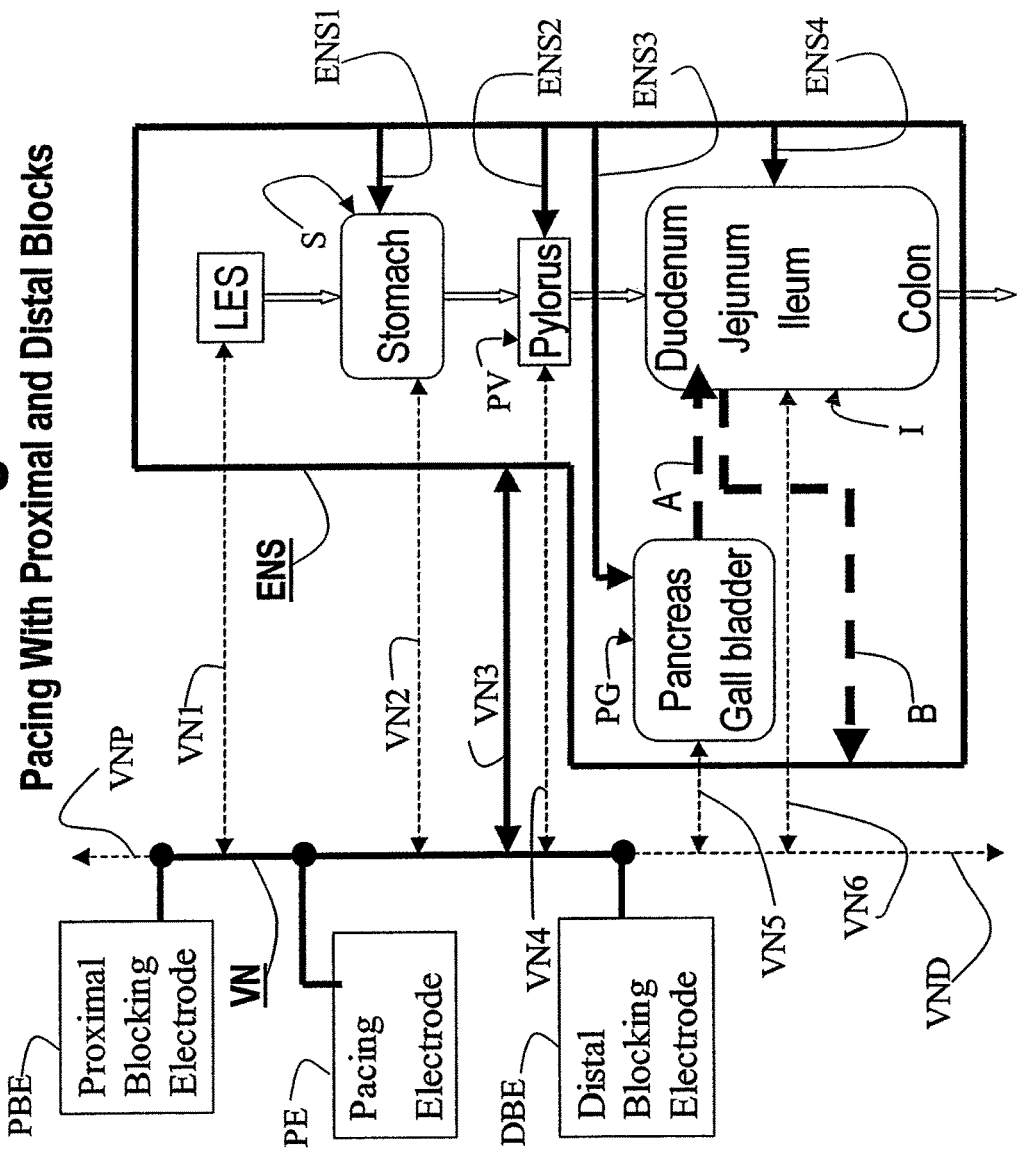
FIG. 7 is the view of FIG. 6 showing the application of a nerve conduction block electrode distal to the pacing electrode.

FIG. 7 illustrates the addition over FIG. 6 of a nerve conductive block DBE distal to the pacing electrode PE. The proximal block PBE prevents adverse events resulting from afferent signals and heightens the GI effectiveness by blocking antidromic interference as discussed with reference to FIG. 6.

In FIG. 7, the distal block DBE is provided in the event there is a desire to isolate the pacing effect of electrode PE. For example, a physician may which to enhance the vagus and enteric activity in the region proximal to the duodenum but may wish to avoid stimulating pancreo-biliary output. For example, a patient may have a GI problem without apparent colon dysfunction (e.g., gastroparesis functional dyspepsia without bowel symptoms). Placing the distal block DBE on a branch of the vagus between the pacing electrode PE and the pancreas and gall bladder PG prevents increased pancreo-biliary output and resultant feedback (illustrated by dotted arrows A and B in FIG. 7 and dotted distal vagal nerve segment VND and vagal trunk VN5).

6. Blocking as an Independent Therapy

Figure 8:
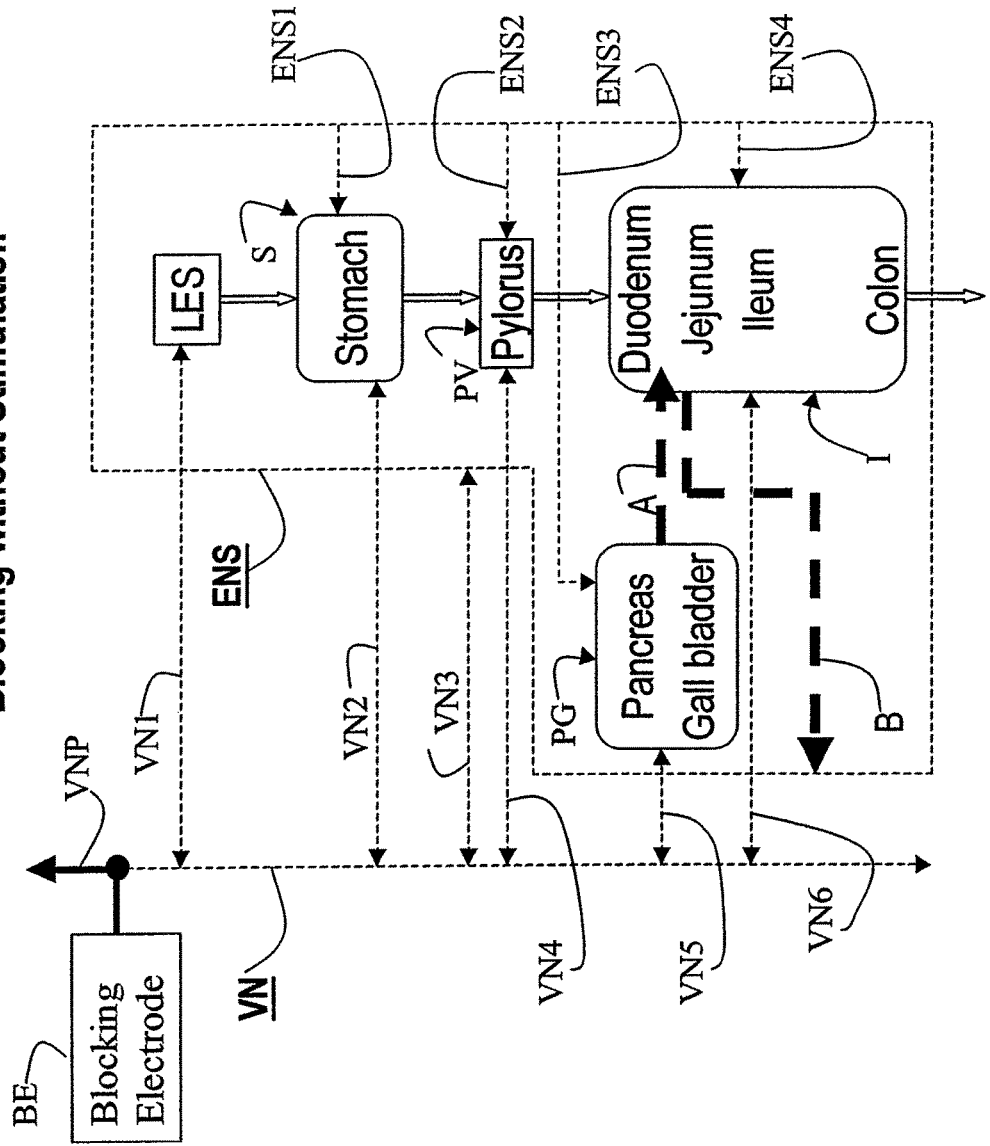
FIG. 8 is the view of FIG. 3 showing the application of a nerve conduction block electrode according to an embodiment of the present invention.

FIG. 8 illustrates an alternative embodiment of the invention.

In certain patients, the vagus nerve may be hyperactive contributing to diarrhea-dominant IBS. Use of a blocking electrode alone in the vagus permits down-regulating the vagus nerve VN, the enteric nervous system ENS and pancreo-biliary output. The block down-regulates efferent signal transmission. In FIG. 8, the hyperactive vagus is illustrated by the solid line of the proximal vagus nerve segment VNP. The remainder of the vagus and enteric nervous system are shown in reduced thickness to illustrate down-regulation of tone. The pancreo-biliary output (and resulting feedback) is also reduced. In FIG. 8, the blocking electrode BE is shown high on the vagus relative to the GI tract innervation (e.g., just below the diaphragm), the sole blocking electrode could be placed lower (e.g., just proximal to pancreo/biliary innervation VN5).

The use of blocking as an independent therapy also permits treatment for pancreatitis by down regulating vagal activity and pancreatic output including pancreatic exocrine secretion. Also, the blocking may be used as a separate treatment for reducing discomfort and pain associated with gastrointestinal disorders or other vagally mediated pain (i.e., somatic pain sensations transmitted along any nerve fibers with pain sensation modulated by vagal afferent fibers). A nerve stimulation to treat pain is described in U.S. patent application publication No. US2003/0144709 to Zabara et al., published Jul. 31, 2003.

It will be appreciated that patient discomfort and pain is a primary complaint associated with many gastrointestinal disorders. As used in the present application (and appended claims), it will be appreciated that a treatment of a gastrointestinal disorder may include a treatment of a patient's perception of pain without any additional functional therapy associated with a gastrointestinal disorder. Vagal blocking as described herein can treat gastrointestinal pain or discomfort (including that associated with Crohn's disease) and chronic somatic pain as well as the inflammatory basis of Crohn's disease. The vagal blocking as described herein can also treat nausea secondary, for example, to chronic cancer chemotherapy.

7. Application to Obesity

The foregoing discussion has been described in a preferred embodiment of treating FGIDs, gastroparesis and GERD. Obesity is also treatable with the present invention.

Recent literature describes potential obesity treatments relative to gut hormone fragment peptide $YY_{3-36}$. See, e.g., Batterham, et al., "Inhibition of Food Intake in Obese Subjects by Peptide YY3-36", *New England J. Med.*, pp. 941-948 (Sep. 4, 2003) and Korner et al., "To Eat or Not to Eat—How the Gut Talks to the Brain", *New England J. Med.*, pp. 926-928 (Sep. 4, 2003). The peptide $YY_{3-36}$(PPY) has the effect of inhibiting gut motility through the phenomena of the ileal brake. Vagal afferents create a sensation of satiety.

The present invention can electrically simulate the effects of PPY by using the vagal block to down-regulate afferent vagal activity to create a desired sensation of satiety. Since the down-regulation does not require continuous blocking signals, the beneficial efferent signals are permitted.

8. Application to Other Therapies

There are numerous suggestions for vagal pacing or stimulation to treat a wide variety of diseases. For example, U.S. Pat. No. 5,188,104 dated Feb. 23, 1993 describes vagal stimulation to treat eating disorders. U.S. Pat. No. 5,231,988 dated Aug. 3, 1993 describes vagal stimulation to treat endocrine disorders. U.S. Pat. No. 5,215,086 dated Jun. 1, 1993 describes vagal stimulation to treat migraines. U.S. Pat. No. 5,269,303 dated Dec. 14, 1993 describes vagal stimulation to treat dementia. U.S. Pat. No. 5,330,515 dated Jul. 19, 1994 describes vagal stimulation to treat pain. U.S. Pat. No. 5,299,569 dated Apr. 5, 1994 describes vagal stimulation to treat neuropsychiatric disorders. U.S. Pat. No. 5,335,657 dated Aug. 9, 1994 describes vagal stimulation to treat sleep disorders. U.S. Pat. No. 5,707,400 dated Jan. 13, 1998 describes vagal stimulation to treat refractory hypertension. U.S. Pat. No. 6,473,644 dated Oct. 29, 2002 describes vagal stimulation to treat heart failure. U.S. Pat. No. 5,571,150 dated Nov. 5, 1996 describes vagal stimulation to treat patients in comas. As previously described, U.S. Pat. No. 5,540,730 dated Jul. 30, 1996 describes vagal stimulation to treat motility disorders and U.S. Pat. No. 6,610,713 dated Aug. 26, 2003 describes vagal stimulation to inhibit inflammatory cytokine production. All of the foregoing U.S. patents listed in this paragraph are incorporated herein by reference.

All of the foregoing suffer from undesired effects of vagal pacing on cardiovascular, gastrointestinal or other organs. Nerve conduction blocking permits longer pulse durations which would otherwise have adverse effects on other organs such as those of the cardiovascular or gastrointestinal systems. In accordance with the present invention, all of the foregoing disclosures can be modified by applying a blocking electrode and blocking signal as disclosed herein to prevent adverse side effects. By way of specific example, pacing a vagus nerve in the thoracic cavity or neck combined with a blocking electrode on the vagus nerve distal to the pacing electrode can be used to treat neuropsychiatric disorders (such as depression and schizophrenia) and Parkinson's and epilepsy and dementia. In such treatments, the blocking electrode is placed distal to the stimulating electrode 25 shown in FIGS. 4 and 2, respectively, of each of U.S. Pat. Nos. 5,269,303 and 5,299,569. The present invention thereby enables the teachings of the afore-referenced patents listed in foregoing two paragraphs.

As described, the parameters of the stimulating and blocking electrodes can be inputted via a controller and, thereby, modified by a physician. Also, FIG. 2 illustrates a feedback for controlling a stimulating electrode. Feedbacks for stimulating electrodes are also described in the patents incorporated by reference. The blocking electrode can also be controlled by an implanted controller and feedback system. For example, physiologic parameters (e.g., heart rate, blood pressure, etc.) can be monitored. The blocking signal can be regulated by the controller to maintain measured parameters in a desired range. For example, blocking can be increased to maintain heart rate within a desired rate range during stimulation pacing.

9. Opportunity for Physician to Alter Treatment for Specific Patient

Gastrointestinal disorders are complex. For many, the precise mechanism of the disorder is unknown. Diagnosis and treatment are often iterative processes. The present invention is particularly desirable for treating such disorders.

Use of proximal and distal blocking electrodes in combination with one or more pacing electrode permits a physician to alter an operating permutation of the electrodes. This permits regional and local up- or down-regulation of the nervous system and organs. Further, pacing parameters (duty cycle, current, frequency, pulse length) can all be adjusted. Therefore, the treating physician has numerous options to alter a treatment to meet the needs of a specific patient.

In addition, a physician can combine the present invention with other therapies (such as drug therapies like prokinetic agents).

D. Alternative Embodiments

1. Background

Figure 9:
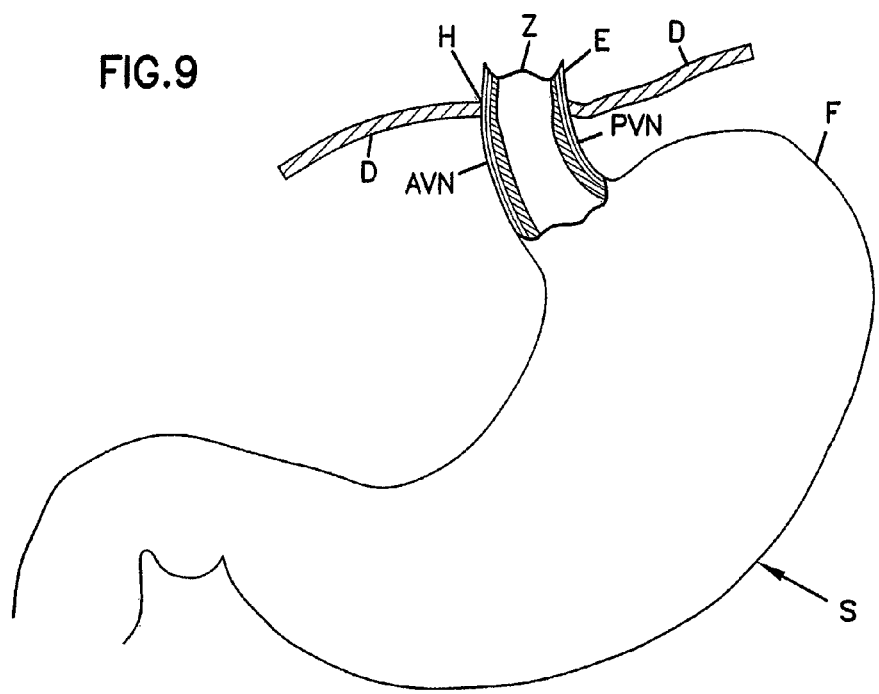
FIG. 9 is a schematic representation of a patients' stomach shown partially in section and illustrating a representative placement of anterior and posterior vagus nerves with respect to the anatomy of the stomach and diaphragm.
Figure 10:
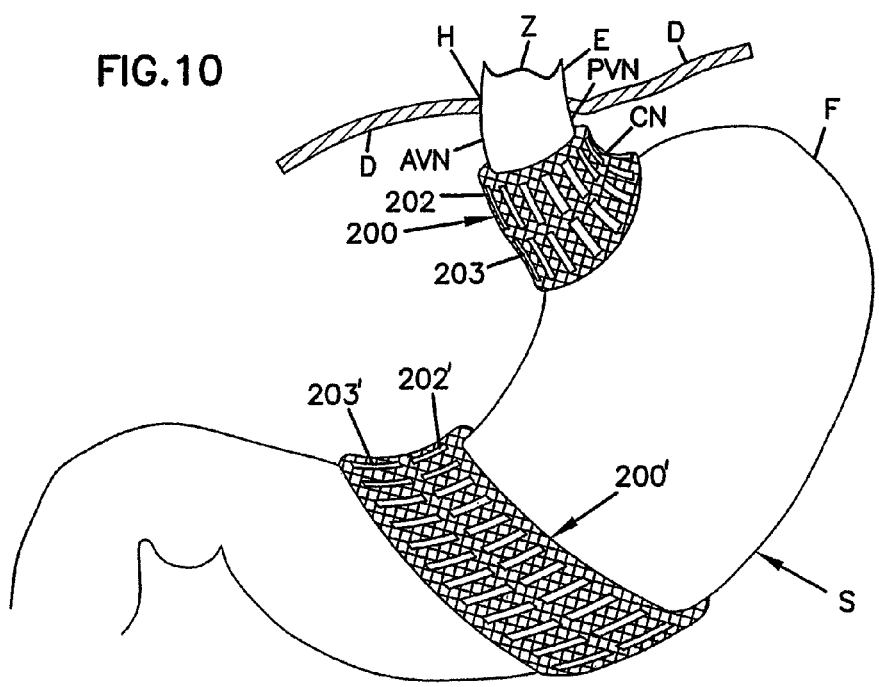
FIG. 10 is the view of FIG. 9 showing a further embodiment of the present invention in utilizing electrode bands.
Figure 11:
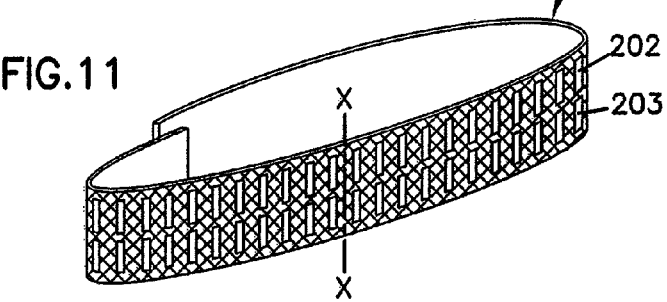
FIG. 11 is a perspective view of a band for use in the embodiment of FIG. 10.
Figure 12:
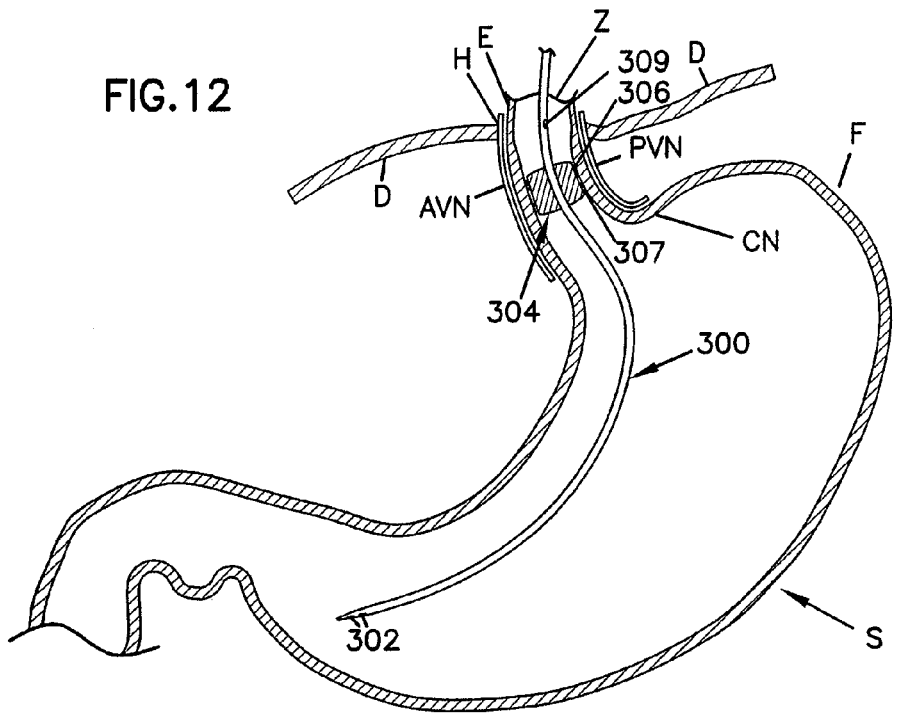
FIG. 12 is a side sectional view of a patients' stomach in illustrating a yet alternative embodiment of the present invention.

With reference to FIG. 9, a stomach S is shown schematically for the purpose of facilitating an understanding of alternative embodiments of the invention as illustrated in FIGS. 10-15. In FIG. 9, the stomach S is shown with a collapsed fundus F which is deflated due to fasting. In practice, the fundus F can be reduced in size and volume (as shown in FIG. 9) or expanded (as shown in FIG. 12).

The esophagus E passes through the diaphragm D at an opening or hiatus H. In the region where the esophagus E passes through the diaphragm D, trunks of the vagal nerve (illustrated as the anterior vagus nerve AVN and posterior vagus nerve PVN) are disposed on opposite sides of the esophagus E. It will be appreciated that the precise location of the anterior and posterior vagus nerves AVN, PVN relative to one another and to the esophagus E are subject to a wide degree of variation within a patient population. However, for most patients, the anterior and posterior vagus nerves AVN, PVN are in close proximity to the esophagus E at the hiatus H where the esophagus E passes through the diaphragm D.

The anterior and posterior vagus nerves AVN, PVN divide into a plurality of trunks that innervate the stomach directly and via the enteric nervous system and may include portions of the nerves which may proceed to other organs such as the pancreas, gallbladder and intestines. Commonly, the anterior and posterior vagus nerves AVN, PVN are still in close proximity to the esophagus E and stomach (and not yet extensively branched out) at the region of the junction of the esophagus E and stomach S.

In the region of the hiatus H, there is a transition from esophageal tissue to gastric tissue. This region is referred to as the Z-line (labeled "Z" in the Figures). Above the Z-line, the tissue of the esophagus is thin and fragile. Below the Z-line, the tissue of the esophagus E and stomach S are substantially thickened and more vascular. Within a patient population, the Z-line is in the general region of the lower esophageal sphincter. This location may be slightly above, slightly below or at the location of the hiatus H.

2. Implanted Band Electrode a. Description of Device

With reference to FIG. 10, a band 200 is shown placed around the esophagus E below the diaphragm D and overlying the anterior and posterior vagus nerves AVN, PVN at the cardiac notch CN. Alternatively, it can be placed completely around the upper portion of the stomach near its junction of the esophagus. Placement of a band 200 around the esophagus E directly beneath the diaphragm D ensures that the band may be placed around the anterior and posterior vagus nerves AVN, PVN without the need for extensive dissection of the nerves AVN, PVN.

The band 200 may be formed of polyester or the like or any other suitable material which may be sutured in place or otherwise fastened in place surrounding the esophagus E or gastric cardia. Preferably, the band 200 is placed at the junction of the esophagus E and stomach S such that the band may overly both the esophagus E and stomach S at the cardiac notch CN.

The band 200 may have a plurality of electrodes which, in the embodiment of FIG. 10 include an upper electrode array 202 and a lower electrode array 203. In the embodiment of FIG. 11 (in which a band 200 is shown lying flat), the electrode arrays 202, 203 are shown with electrodes placed at an angle relative to the cylindrical axis X-X of the band 200.

Placement of the band 200 as described ensures that at least a subset of the electrodes 202, 203 will be in overlying relation to the anterior and posterior vagus nerves AVN, PVN. As a result, energizing the electrodes 202, 203 will result in stimulation of the anterior and posterior vagus nerves AVN, PVN and/or their branches.

In therapeutic applications, the upper array 202 of electrodes may be connected to a blocking electrical signal source (with a blocking frequency and other parameters as previously described) and the lower array 203 of electrodes may be connected to a stimulation electrical signal source as previously described. Of course, only a single array of electrodes could be used with all electrodes connected to either a blocking or a stimulating signal.

The electrical connection of the electrodes 202, 203 to a controller is not shown but may be as previously described by having a leads connecting the electrodes directly to an implantable controller. Alternatively, and as previously described, electrodes may be connected to an implanted antenna for receiving a signal to energize the electrodes.

The use of an array of electrodes permits the collar 200 to be placed without the need for great accuracy at the time of placement. In the event it is desirable that electrodes not directly overlying a vagus nerve be deactivated, the electrodes could, through operation of a controller, be individually energized to detect a physiological response. The absence of a physiological response (other than possible muscular action of the stomach and esophagus) would indicate the absence of an overlying relation to a vagus nerve. The presence of a physiological response would indicate overlying relation of the tested electrode to a vagus nerve.

By identifying which electrodes create a physiologic response, the remaining electrodes (i.e., those not having a physiological response) could be permanently deactivated. An example of a physiological response would be a cardiovascular response which may be attributed to a signal of about 2-80 hertz and up to 50 milliamps and as more fully described in U.S. Pat. No. 6,532,388 to Hill et al dated Mar. 11, 2003. As a result, a selected one of the AVN or PVN could be energized.

It will be appreciated the foregoing description of identifying electrodes to be deactivated is a non-limiting embodiment. For example, all electrodes could be energized. The therapies as previously described could be employed by using blocking electrodes or stimulation electrodes or both in order to block or energize (or both) the vagus nerve.

FIG. 10 also illustrates an alternative embodiment in the form of a band 200' surrounding the body of the stomach S and having arrays 202', 203'. Since the band 200' is more distal to the esophagus E, different and more distal trunks of the vagus nerves would be energized. Also, such a placement would permit the option of covering the anterior vagus nerve while not covering the posterior vagus nerve (or visa versa).

With the embodiment shown in FIG. 10, the benefits of vagal stimulation with resulting enteric rhythm management and the aforementioned benefits of blocking can be achieved without the need for extensive dissection of the vagus nerve. Further, the benefits can be achieved without the need for directly clamping electrodes on a vagus nerve, thereby reducing the possibility of injury to a vagus nerve.

In addition to the benefits of nerve stimulation, the band 200 can also be used to restrict and potentially lengthen the esophagus thereby reducing possibilities for reflux as more fully described in commonly assigned and co-pending U.S. patent application Ser. No. 10/600,088 filed Jun. 20, 2003 and entitled "Gastro-Esophageal Reflux Disease" (GERD) Treatment Method and Apparatus" (published Dec. 23, 2004 as Publication No. US 2004/0260316 A1).

b. Application to Obesity and Satiety

The embodiment of FIG. 10 is particularly suitable for the treatment of obesity. Obesity is of epidemic proportions and is associated with large decreases in life expectancy and early mortality. Peeters, et al., "Obesity in Adulthood and Its Consequences for Life Expectancy: A Life Table Analysis", *Annals of Internal Medicine*, Vol. 138, No. 1, pp. 24-32 (2003).

In the embodiment of FIG. 10, the upper band 200 is placed around the stomach near the cardiac notch CN. Electrode array 202 may be de-activated (or not present on the band 200). Lower array 203 can be energized with a blocking signal.

The prior art suggests stimulating the vagus with a stimulating signal for treating obesity or eating disorders. See, e.g., U.S. Pat. No. 5,188,104 to Wernicke et al., dated Feb. 23, 1993; U.S. Pat. No. 5,263,480 to Wernicke et al., dated Nov. 23, 1993; U.S. Pat. No. 6,587,719 to Barrett et al., dated Jul. 1, 2003 and U.S. Pat. No. 6,609,025 to Barrett et al., dated Aug. 19, 2003. These patents all describe stimulating, non-blocking signals (e.g., stimulating to a level slightly below a so-called "retching threshold" as described in the '025 patent). As such, all fail to note the problem associated with obesity and eating discords that is not addressed by stimulating the vagus but, rather, by blocking stimulation on the vagus.

The blocking at cardiac notch CN reduces fundal accommodation and creates satiety sensations. Such a physiologic response is suggested by vagotomy data in which truncal vagotomy patients have experienced weight loss and increased satiety. See, e.g., Kral, "Vagotomy as a Treatment for Morbid Obesity", *Surg. Clinics of N. Amer.*, Vol. 59, No. 6, pp. 1131-1138 (1979), Gortz, et al., "Truncal Vagotomy Reduces Food and Liquid Intake in Man", *Physiology & Behavior*, Vol. 48, pp. 779-781 (1990), Smith, et al., "Truncal Vagotomy in Hypothalamic Obesity", *The Lancet*, pp. 1330-1331 (1983) and Kral, "Vagotomy for Treatment of Severe Obesity", *The Lancet*, pp. 307-308 (1978).

The optional lower band 200' is placed lower on the stomach (e.g., close to the pylorus). The lower electrode array 203' of the lower band 200' is energized with a stimulation signal to modulate intestinal motility in the event motility is otherwise impaired by the upper band blocking.

The upper array 202' of the lower band 200' is energized with a blocking signal so that the stimulation signal at electrodes 203' does not interfere with the blocking effect of electrodes 203 of upper band 200. In this obesity treatment, the electrodes of the bands 200, 200' can be placed on constricting bands (such as the well-known Lap-Band® system of Inamed Inc., Santa Barbara, Calif., USA, and used in obesity treatment). More preferably, the bands 200, 200' are not constricting thereby minimizing erosion risks otherwise associated with highly constricting bands. However, the neural blocking technology of the present invention can be incorporated into such constricting bands or used in conjunction other obesity surgeries or therapies. Specifically, the scientific literature indicates a vagotomy in combination with other obesity procedure (e.g., antrectomy, gastroplasty and biliopancreatic bypass) improves weight loss procedures. Tzu-Ming, et al., "Long-Term Results of Duodenectomy with Highly Selective Vagotomy in the Treatment of complicated Duodenal Ulcers", *Amer. J. of Surg.*, Vol. 181, pp. 372-376 (2001), Kral, et al., "Gastroplasty for Obesity: Long-Term Weight Loss Improved by Vagotomy", *World J. Surg.*, Vol. 17, pp. 75-79 (1993), and Biron, et al., "Clinical Experience with Biliopancreatic Bypass and Gastrectomy or Selective Vagotomy for Morbid Obesity", *Canadian J. of Surg.*, Vol. 29, No. 6, pp. 408-410 (1986).

Vagal neural blocking simulates a vagotomy but, unlike a vagotomy, is reversible and controllable. Therefore, while obesity is particularly described as a preferred treatment, the vagal neural block of the present invention can be used as a less drastic procedure for treatments previously performed with a vagotomy. Without limitation, these include obesity, ulcers or chronic pain or discomfort (alone or in combination with conjunctive procedures).

Further, bulimia has been identified as a disease amenable to treatment by decreasing afferent vagal activity via pharmacological vagal inhibitors delivered systemically. Faris, et al., "Effect of Decreasing Afferent Vagal Activity with Ondansetron on Symptoms of Bulimia Nervosa: a Randomized, Double-Blind Trial", *The Lancet*, pp. 792-797 (2000). Therefore, bulimia and other diseases treatable with vagal blocker drugs can be treated with the targeted and site-specific vagal neural block of the present invention.

3. Acute Treatment Device a. Device Description

FIG. 12 illustrates a still further embodiment of the present invention where a nasogastric tube 300 is passed into the stomach. It will be appreciated that nasogastric tubes are well known and form no part of this invention per se. Some nasogastric tubes have specialized functions. An example is a tamponade tube having gastric and esophageal balloons. An example of such is the Bard® Minnesota Four Lumen Esophagogastric Tamponade Tube for the Control of Bleeding from Esophageal Varices as described in product literature (information for use) contained with the product of that name dated 1998 by C. R. Bard, Inc., Covington, Ga., USA. Further, while a nasogastric tube is a preferred embodiment other devices (e.g., an orogastric tube or any elongated device to position electrodes near the esophagus/stomach junction) could be used. Also, while placement at the esophagus/stomach junction is preferred, the device can be placed in a different lumen (e.g., the trachea) for transmucosal stimulation.

The nasogastric tube 300 is multi-lumen tube which includes distal openings 302 to which suction can be applied to remove gastric contents through the tube 300. A compliant balloon 304 surrounds the gastric tube. Proximal to the balloon 304 is an opening 309 in communication with a lumen (not shown) to which a suction can be applied to remove saliva through the opening 309.

Figure 14:
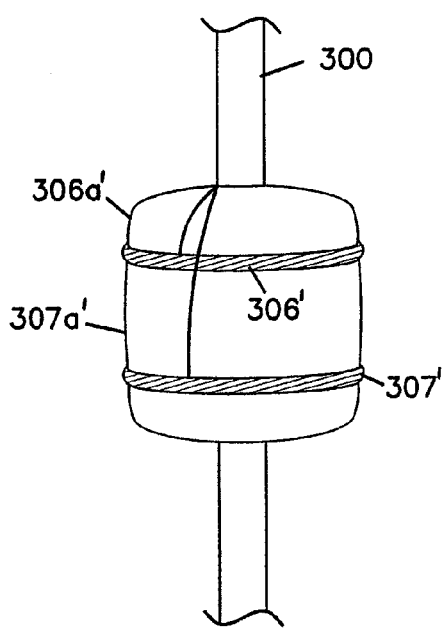
FIG. 14 is a side elevation view of an alternative embodiment of a balloon portion of an apparatus for use in the embodiment of FIG. 12.
Figure 13:
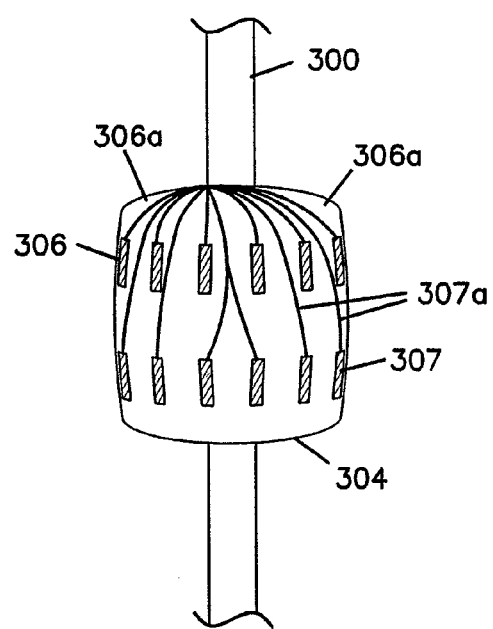
FIG. 13 is a side elevation view of a balloon portion of an apparatus for use in the embodiment of FIG. 12.

The balloon 304 has a plurality of electrodes which may include an upper array 306 of electrodes and a lower array 307 of stimulation electrodes. The electrodes of the upper array 306 may be connected to a blocking signal source via conductors 306a (FIG. 13). The electrodes of the lower array 307 may be connected to a stimulation signal source via conductors 307a. The conductors 306a, 307a may be passed through a lumen in the tube 300 to an external controller (not shown). As a result, multiple electrodes can be energized for transmucosal stimulation of the anterior and posterior vagus nerves AVN, PVN. FIG. 14 shows an alternative design where the arrays 306, 307 are replaced with expandable, circumferential electrodes 306', 307' connected to a controller (not shown) by conductors 306a', 307a'.

As in the embodiment of FIG. 10, the individual electrodes of the arrays 306, 307 may optionally be selectively energized to detect a cardiovascular signal indicating an electrical coupling of the electrodes to the vagus nerves AVN, PVN. Electrodes that do not create such a coupling may optionally be deactivated such that only the electrodes having an effective coupling with the vagus nerves AVN, PVN will be activated. Also, and as in the embodiment of FIG. 10, there may be a single array of electrodes or all electrodes may be energized with either a blocking or stimulation signal.

It will be noted in this embodiment that the electrodes are disposed abutting the mucosal surface of the esophageal and stomach lining and are not in direct contact with the vagus nerves AVN, PVN. Instead, the electrodes are spaced from the vagus nerves AVN, PVN by the thickness of the stomach and lower esophageal wall thickness.

Transmucosal electrical stimulation of nerves is well known. Such stimulation is disclosed in U.S. Pat. No. 6,532,388 to Hill et al dated Mar. 11, 2003 (describing transmucosal stimulation of nerves across a trachea using a balloon with electrodes in the trachea to modulate cardiac activity). Also, the phenomena of transmucosal electrical stimulation of nerves is described in Accarino, et al, "Symptomatic Responses To Stimulation Of Sensory Pathways In The Jejunum", *Am. J. Physiol.*, Vol. 263, pp. G673-G677 (1992) (describing afferent pathways inducing perception selectively activated by transmucosal electrical nerve stimulation without disruption of intrinsic myoelectrical rhythm); Coffin, et al, "Somatic Stimulation Reduces Perception Of Gut Distention In Humans", *Gastroenterology*, Vol. 107, pp. 1636-1642 (1994); Accarino, et al, "Selective Dysfunction Of Mechano Sensitive Intestinal Afferents In Irritable Bowel Syndrome", *Gastroenterology*, Vol. 108, pp. 636-643 (1994), Accarino, et al "Modification Of Small Bowel Mechanosensitivity By Intestinal Fat", *GUT*, Vol. 48, pp. 690-695 (2001); Accarino, et al, "Gut Perception In Humans Is Modulated By Interacting Gut Stimuli", *Am. J. Physiol. Gastrointestinal Liver Physiol.*, Vol. 282, pp. G220-G225 (2002) and Accarino, et al, "Attention And Distraction Colon Affects On Gut Perception", *Gastroenterology*, Vol. 113, pp. 415-442 (1997).

Figure 15:
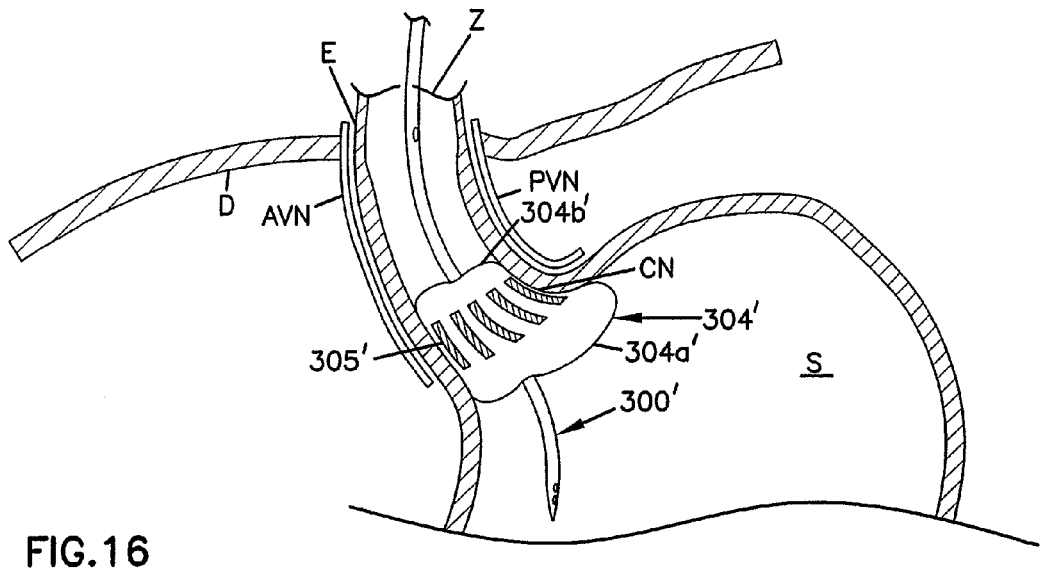
FIG. 15 is a side sectional view of a patients' stomach in illustrating a yet alternative embodiment of the invention of FIG. 12.
Figure 16:
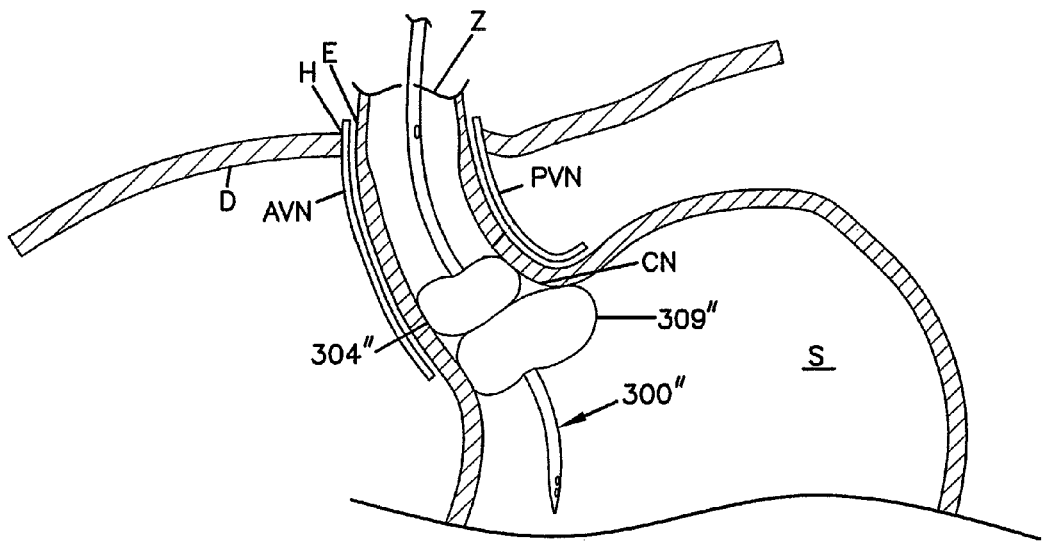
FIG. 16 is a side sectional view of a patients' stomach in illustrating a still further alternative embodiment of the invention of FIG. 12.

Alternative embodiments of the transmucosal stimulation device of FIG. 12 are shown in FIGS. 15 and 16. In FIG. 15, the balloon 304' is conical in shape with a base end 304a' placed distally on the tube 300'. After expansion, the base end 304a' expands within the stomach S. The physician then pulls on the tube 300'. The base end 304a' (which is larger in diameter than the esophagus E) abuts the stomach S at the cardiac notch CN acting as a stop. This insures the electrodes 305' (only a single array is shown for ease of illustration) abuts the mucosal tissue at the junction of the stomach S and esophagus E. The electrodes 305' are on the narrow end 304b' of the balloon 304' and expansion of the balloon 304' ensures contact of the electrodes with the mucosal tissue.

FIG. 16 illustrates an embodiment using two balloons 304" and 309". The distal balloon 309", when expanded, is larger than the esophagus E and acts as a stop when the physician pulls on the tube 300". The electrodes 305" are on a smaller balloon 304" which may expand in the esophagus E. The balloon 304", 309" are positioned for the electrodes 305" to be against the mucosal tissue at the junction of the stomach S and esophagus E when the distal balloon 309" abuts the cardiac notch CN and the proximal balloon 304" is expanded. The electrodes may be positioned to be completely within the stomach to reduce risk of injury to esophageal tissue. More conveniently, a tube such as the afore-mentioned Bard® tube may be modified for electrodes to be placed on the proximal side of the gastric balloon.

In all of the foregoing, a balloon is expanded to urge the electrodes against the mucosal tissue. While this is a presently preferred embodiment, any mechanism for urging the electrodes against the mucosal tissue may be used. In each of FIGS. 15 and 16, the tube 300', 300" is shown as it passes through the balloons 304', 304" and 309". This illustration is made to indicate the tube passes through the balloons and does terminate at the balloons. In fact, as the tube 300', 300" passes through the balloons 304', 304" and 309" it would be surrounded by the material of the balloons 304', 304" and 309" and would not be visible.

Figure 17:
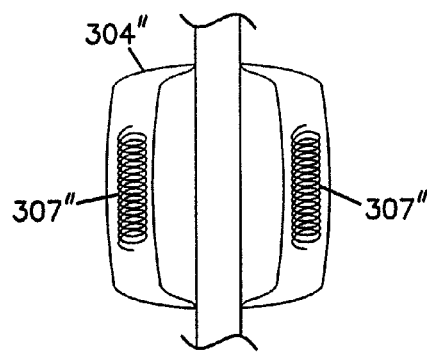
FIG. 17 is a schematic view of a balloon with magnetic coils.

A still further embodiment is shown in FIG. 17. Instead of directly stimulating with current, the nerves are stimulated with magnetic fields. In this case, the electrodes are coils 307' insulated within the balloon 304'. The coils 307''' create magnetic fields which inductively couple with the vagus nerves to create the blocking and stimulating impulses within the nerves.

b. Application to Acute Pancreatitis

When energized with a blocking frequency, the embodiment of FIG. 13 is useful for treating acute or recurrent pancreatitis. This extremely serious disease is characterized by an over-active pancreas which excretes digestive enzymes to such an extent that the pancreas itself is digested. The disease can be extremely painful. In many cases, the disease is fatal. The number of US patients who suffer an episode of acute pancreatitis is approximately 185,000 annually. Baron, et al., "Acute Necrotizing Pancreatitis", *New England J. of Medicine*, Vol. 340, No. 18, pp. 1412-1417 (1999). This high incidence, coupled with the cost and length of stay required, make the total cost of this disease to society enormous. No definitive therapy is currently available to treat these patients except supportive care. Furthermore, the overall mortality rate for severe pancreatitis is about 20 to 30%. Id.

A recent study reported that the average total hospital cost to obtain a survivor of severe, acute pancreatitis is nearly $130,000 with an average length of hospital stay of 40 days. Soran, et al., "Outcome and quality of life of patients with acute pancreatitis requiring intensive care", *J. Surg. Res.*, 91(1), pp. 89-94 (2000). Further complicating the management of these patients is the uncertainty surrounding the prognosis because the course of the disease is unpredictable at initial presentation. Chatzicostas, et al., "Balthazar computed tomography severity index is superior to Ranson criteria and APACHE II and II scoring systems in predicting acute pancreatitis outcome", *J. Clinical Gastroenterology*, 36(3), pp. 253-260 (2003). If patients could be successfully treated during the initial phases of the disease, with a higher survival rate, there is a high probability of returning to a productive life. Soran, et al., supra.

Pancreatitis may be associated with a number of etiologies including chronic alcoholism or gallstones (e.g., gallstones lodged in the pancreatic or common duct). When acute pancreatitis becomes severe, treatment options are severely limited. Morbidity and mortality rates for pancreatitis are sobering. Baron, et al., "Acute Necrotizing Pancreatitis", *New England J. of Medicine*, Vol. 340, No. 18, pp. 1412-1417 (1999) and Steer et al., "Chronic Pancreatitis", *New England J. of Medicine*, pp. 1482-1490 (1995).

Down-regulating vagal activity can be used to treat pancreatitis. A recently reported finding in experimental pancreatitis demonstrated that the vagus nerves are strongly implicated in the pathophysiology of pancreatitis. Yoshinaga, et al., "Cholecystokinin Acts as an Essential Factor in the Exacerbation of Pancreatic Bile Duct Ligation-Induced Rat Pancreatitis Model Under Non-Fasting Condition", *Japanese J. Pharmacol*, Vol. 84, pp. 44-50 (2000). Pharmacologic means of decreasing pancreatic secretion have been attempted with limited success because of the dose-limiting side effects encountered with the drugs, their lack of specificity or their lack of availability. In fact, one recent trial of a specific blocker of parasympathetic (vagus nerves) control of secretion demonstrated a shortened recovery period in patients with acute pancreatitis while trials with other pancreatic down-regulating drugs that are less specific or potent have proven to be disappointing. Zapater, et al., "Do Muscarinic Receptors Play a Role in Acute Pancreatitis?", *Clin. Drug Invest.*, 20(6), pp. 401-408 (2000); Norton, et al., "Optimizing Outcomes in Acute Pancreatitis", *Drugs*, 61(11), pp. 1581-1591 (2001). Atropine is a drug that blocks parasympathetic nerve endings. It is known to be desirable to use atropine in acute pancreatitis patients to down-regulate pancreatic activity. Unfortunately, for most such patients, this drug cannot be used due to its many side effects.

Acute pancreatitis patients may be placed on intravenous feeding with the device 300 left in place for a chronic length of time (e.g., several days or weeks). At least the electrodes of the lower array 307 may be energized with a blocking signal for the treatment of acute pancreatitis. The invention permits down-regulation of pancreatic output through vagal blocking without the need for undesirable surgery for direct vagal access.

In addition to utility for treating pancreatitis, the present invention may be used to avoid pancreatitis in patients having an increased likelihood of developing the disease. For example, patients undergoing endoscopic retrograde cholangiopancreatography (ERCP) and/or related procedures are known to having a higher likelihood of developing pancreatitis. Such patients may be treated with the present invention with a blocking signal to down-regulate pancreatic output and reduce the likelihood of developing pancreatitis.

Many physicians treating patients with pancreatitis use a nasogastric tube as part of the treatment. As a result, the present invention is illustrated as being incorporated on a nasogastric tube. However, a significant body of physicians adheres to a belief that pancreatitis patients benefit from a feeding involving placing nourishment directly into the jejunum portion of the small intestine via a naso jejunal tube. While the present invention is illustrated in an embodiment of placement of the balloon and electrodes on a naso-gastric tube, the invention can also be placed on a nasojejunal tube or a nasogastricjejunal tube.

c. Application to Ileus

With the device of FIGS. 12-16, the distal electrodes 307 may be energized with a stimulation frequency as described for treatment of ileus. Post-trauma and post-surgery, patients may experience ileus which is a dysfunction of the GI tract characterized in part by a lack of motility through the intestines. Prolonged ileus can result in stasis and serious infection. Kaiser, "Gallstone Ileus", *New England J. of Medicine*, Vol. 336, No. 12, pp. 879-880 (1997) (correspondence), Taguchi, et al., "Selective Postoperative Inhibition of Gastrointestinal Opioid Receptors", *New England J. of Medicine*, Vol. 345, No. 13, pp. 935-940 (2001) and Steinbrook, "An Opioid Antagonist For Postoperative Ileus", *New England J. of Medicine*, Vol. 345, No. 13, pp. 988-989 (2001) (Editorial).

Ileus patients commonly have nasogastric tubes as a regular part of their hospital stay. Without additional invasiveness, the present invention can be used as the nasogastric tube with the addition of stimulation electrodes to stimulate the vagus to enhance motility.

The embodiment of FIG. 12 would permit the lower electrodes 307 to be energized for stimulation frequency to treat ileus. Optionally, the upper electrodes 306 can be energized for blocking frequency if needed to prevent antidromic inhibitory responses or to prevent undesired cardiac response.

The embodiment of FIG. 12-16 is useful to permit a diagnosis for a surgical implants as described in foregoing embodiments. Namely, responsiveness of a patient's gastrointestinal symptoms (such as IBS) to the embodiment of FIG. 12 could justify a more invasive surgical placement of electrodes directly on the anterior or posterior vagus nerves.

In FIG. 15, a blocking or stimulating signal can be applied to the electrode 305'. A blocking frequency is anticipated to be a therapeutic value for treating, for example, acute pancreatitis or an exacerbation of chronic pancreatitis. A stimulating frequency is anticipated to be of therapeutic value for treating ileus. With the embodiment of FIG. 12, ileus, for example, can be treated by applying a stimulation frequency to the lower electrode 307. A blocking frequency to the upper electrode 306 can be used to block antidromic responses or to block adverse side effects of the stimulation signal on proximal organs (e.g., cardiac responses).

4. Diagnostic Device

Figure 18:
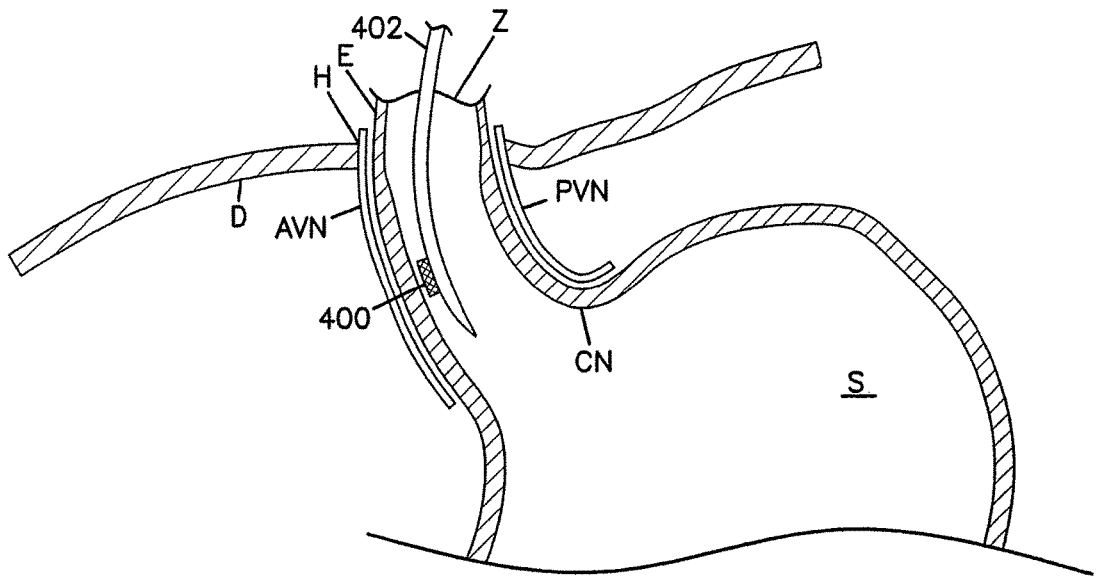
FIG. 18 is a side sectional view of the esophagus and stomach junction and illustrating a yet further embodiment of the present invention.

FIG. 18 illustrates a still further embodiment of the present invention where a stimulating electrode 400 is placed near a distal end of an esophageal gastric duodenal (EGD) scope 402. Leads (not shown) pass through the scope 402 connecting the electrode 400 to a controller (not shown).

Stimulation may be applied via the electrode 400 for transmucosal stimulation of an opposing vagus nerve (AVN in FIG. 18). Proper placement to achieve stimulation can be identified through the previously described techniques of identifying a cardiovascular response to the stimulation indicating appropriate opposition of the electrode 400 to a vagus nerve.

Figure 19:
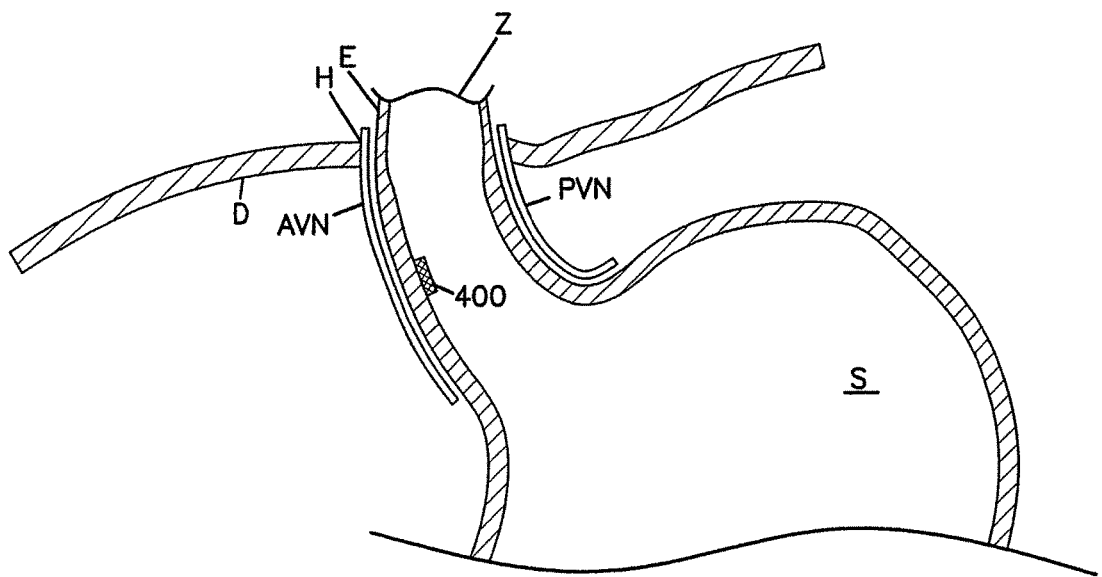
FIG. 19 is a view similar to that of FIG. 15 and illustrating an alternative embodiment of the invention shown in FIG. 15.

The scope may be left in place or may be removed by placing the electrode attached to the mucosal wall (FIG. 19) through a pigtail or other attachment (such as an adhesive) with leads passing through the nostril or mouth. Alternatively, the electrode 400 may be kept in place positioned underneath the mucosal layer and may be energized by radio frequencies applied externally.

It will be appreciated that attachment of electrical apparatus to internal mucosal layers of patients' is well known. Such a system is described with respect to the Bravo™ pH monitoring system of Medtronic, Inc., Minneapolis, Minn., USA and as described in its product literature UC 200300235 EN N15344 (2002) titled "Bravo™ pH Monitoring System Catheter-Free pH Testing".

The foregoing embodiment is particularly useful for identifying patients responsive to blocking and stimulation as a diagnostic before applying a more invasive procedure using the blocking and stimulation apparatus and methods described herein.

With the foregoing detailed description of the present invention, it has been shown how the objects of the invention have been attained in a preferred manner. Modifications and equivalents of disclosed concepts such as those which might readily occur to one skilled in the art, are intended to be included in the scope of the claims which are appended hereto.

We claim:

1. A system for treating obesity comprising:
   a) a posterior electrode and an anterior electrode adapted to be placed on a vagus nerve at a subdiaphragmatic location;
   b) an implantable controller electrically connected to each of the posterior electrode and anterior electrode; the implantable controller comprising an induction coil, an anterior and a posterior electrical signal generator, a battery, and a central processing unit comprising program storage and memory;
   c) an external controller comprising an external coil inductively coupled to the induction coil, wherein the external controller is configured to communicate at least one parameter for a neural conduction blocking signal to the implantable controller, wherein the at least one parameter is selected for the neural conduction blocking signal to i) at least partially downregulate the vagus nerve, ii) allow at least partial recovery of the nerve activity following discontinuation of the neural conduction blocking signal, and iii) reduce pancreatic and biliary output via inhibition of pancreo-biliary output.

2. The system of claim 1, wherein the parameter is a frequency of at least 500 Hz.

3. The system of claim 2, wherein the parameter is application of the signal intermittently.

4. The system of claim 1, wherein the central processing unit stores the at least one parameter.

* * * * *